US007731737B2

(12) United States Patent
DiPoto

(10) Patent No.: US 7,731,737 B2
(45) Date of Patent: Jun. 8, 2010

(54) METHODS AND APPARATUSES FOR FIXATION OF THE SPINE THROUGH AN ACCESS DEVICE

(75) Inventor: Gene DiPoto, Upton, MA (US)

(73) Assignee: Zimmer Spine, Inc., Minneapolis, MN (US)

( * ) Notice: Subject to any disclaimer, the term of this patent is extended or adjusted under 35 U.S.C. 154(b) by 1563 days.

(21) Appl. No.: 10/693,663

(22) Filed: Oct. 24, 2003

(65) Prior Publication Data
US 2005/0090833 A1    Apr. 28, 2005

(51) Int. Cl.
*A61B 17/88*    (2006.01)

(52) U.S. Cl. .................. 606/279; 606/247; 606/198; 606/99; 606/86 A

(58) Field of Classification Search .................. 604/104, 604/106; 606/108, 99, 104, 323, 246–279, 606/198, 86 A; 600/219, 220, 222
See application file for complete search history.

(56) References Cited

U.S. PATENT DOCUMENTS

| 3,789,852 | A | 2/1974 | Kim et al. |
|---|---|---|---|
| 4,545,374 | A | 10/1985 | Jacobson |
| 4,601,713 | A | 7/1986 | Fuqua |
| 4,716,901 | A | 1/1988 | Jackson et al. |
| 4,819,620 | A | 4/1989 | Okutsu |
| 4,863,133 | A | 9/1989 | Bonnell |
| 4,921,478 | A | 5/1990 | Solano et al. |
| 4,984,564 | A | 1/1991 | Yuen |
| 5,025,778 | A | 6/1991 | Silverstein et al. |
| 5,131,382 | A | 7/1992 | Meyer |
| 5,139,499 | A | 8/1992 | Small et al. |
| 5,163,949 | A | 11/1992 | Bonutti |
| 5,171,279 | A | 12/1992 | Mathews |
| 5,190,561 | A | 3/1993 | Graber |
| 5,195,541 | A | 3/1993 | Obenchain |
| 5,196,015 | A | * | 3/1993 | Neubardt ................ 606/61 |
| 5,197,971 | A | 3/1993 | Bonutti |
| 5,224,680 | A | 7/1993 | Greenstein et al. |
| 5,287,845 | A | 2/1994 | Faul et al. |

(Continued)

FOREIGN PATENT DOCUMENTS

EP    0528562 A2    2/1993

(Continued)

OTHER PUBLICATIONS

U.S. Appl. No. 10/658,736, filed Sep. 9, 2003.

(Continued)

*Primary Examiner*—Thomas C Barrett
*Assistant Examiner*—James L. Swiger
(74) *Attorney, Agent, or Firm*—Crompton, Seager & Tufte, LLC

(57) ABSTRACT

In a method of treating the spine of a patient, an access device is inserted into the patient with the access device in a first configuration having a first cross-sectional area at a distal portion thereof. The access device is actuated to a second configuration having an enlarged cross-sectional area at the distal portion thereof such that the distal portion extends across at least a portion of each of two adjacent vertebrae. A stabilization of the vertebrae is then achieved using either translaminar facet screw fixation or transfacet pedicle screw fixation.

26 Claims, 28 Drawing Sheets

U.S. PATENT DOCUMENTS

| | | | |
|---|---|---|---|
| 5,295,994 A | 3/1994 | Bonutti | |
| 5,312,417 A | 5/1994 | Wilk | |
| 5,345,927 A | 9/1994 | Bonutti | |
| 5,354,302 A | 10/1994 | Ko | |
| 5,357,983 A * | 10/1994 | Mathews | 128/898 |
| 5,370,674 A | 12/1994 | Farrell | |
| 5,395,317 A | 3/1995 | Kambin | |
| 5,439,464 A | 8/1995 | Shapiro | |
| 5,454,365 A | 10/1995 | Bonutti | |
| 5,472,426 A | 12/1995 | Bonati | |
| 5,484,437 A | 1/1996 | Michelson | |
| 5,489,307 A | 2/1996 | Kuslich et al. | |
| 5,520,607 A | 5/1996 | Frassica et al. | |
| 5,571,072 A | 11/1996 | Kronner | |
| 5,575,754 A | 11/1996 | Konomura | |
| 5,601,590 A | 2/1997 | Bonutti et al. | |
| 5,601,690 A | 2/1997 | Gauld et al. | |
| 5,667,520 A | 9/1997 | Bonutti | |
| 5,690,606 A | 11/1997 | Slotman | |
| 5,707,359 A | 1/1998 | Bufalini | |
| 5,792,044 A | 8/1998 | Foley et al. | |
| 5,795,289 A | 8/1998 | Wyttenbach | |
| 5,827,319 A | 10/1998 | Carlson et al. | |
| 5,946,988 A | 9/1999 | Metz-Stavenhagen | |
| 5,954,635 A | 9/1999 | Foley et al. | |
| 5,961,499 A | 10/1999 | Bonutti et al. | |
| 5,997,508 A | 12/1999 | Lunn et al. | |
| 6,053,907 A | 4/2000 | Zirps | |
| 6,120,437 A | 9/2000 | Yoon et al. | |
| 6,162,236 A | 12/2000 | Osada | |
| 6,171,299 B1 | 1/2001 | Bonutti | |
| 6,187,000 B1 | 2/2001 | Davison et al. | |
| 6,193,715 B1 | 2/2001 | Wrublewski | |
| 6,306,170 B2 | 10/2001 | Ray | |
| 6,312,443 B1 | 11/2001 | Stone | |
| 6,338,730 B1 | 1/2002 | Bonutti et al. | |
| 6,358,226 B1 | 3/2002 | Ryan | |
| 6,358,266 B1 | 3/2002 | Bonutti | |
| 6,361,488 B1 | 3/2002 | Davison et al. | |
| 6,371,968 B1 | 4/2002 | Kogasaka et al. | |
| 6,383,195 B1 | 5/2002 | Richard | |
| 6,485,518 B1 * | 11/2002 | Cornwall et al. | 623/17.11 |
| 6,494,893 B2 | 12/2002 | Dubrul et al. | |
| 6,497,654 B1 | 12/2002 | Leonard et al. | |
| 6,524,320 B2 | 2/2003 | DiPoto | |
| 6,530,880 B2 | 3/2003 | Pagliuca | |
| 6,530,926 B1 * | 3/2003 | Davison | 606/61 |
| 6,540,747 B1 | 4/2003 | Marino | |
| 6,564,078 B1 | 5/2003 | Marino et al. | |
| 6,652,553 B2 | 11/2003 | Davison et al. | |
| 6,800,084 B2 | 10/2004 | Davison et al. | |
| 6,821,243 B2 | 11/2004 | Pagliuca et al. | |
| 6,837,889 B2 | 1/2005 | Shluzas | |
| 7,004,947 B2 | 2/2006 | Shluzas et al. | |
| 7,056,321 B2 | 6/2006 | Pagliuca et al. | |
| 7,066,937 B2 | 6/2006 | Shluzas | |
| 7,144,393 B2 | 12/2006 | DiPoto et al. | |
| 7,226,451 B2 | 6/2007 | Shluzas et al. | |
| 2001/0011170 A1 | 8/2001 | Davison et al. | |
| 2001/0049498 A1 | 12/2001 | Davison et al. | |
| 2002/0002360 A1 | 1/2002 | Orth et al. | |
| 2003/0009130 A1 | 1/2003 | Stecker et al. | |
| 2003/0014068 A1 | 1/2003 | Bonutti et al. | |
| 2003/0040656 A1 | 2/2003 | Pagliuca et al. | |
| 2003/0073998 A1 | 4/2003 | Pagliuca et al. | |
| 2003/0139648 A1 | 7/2003 | Foley et al. | |
| 2003/0153911 A1 | 8/2003 | Shluzas | |
| 2003/0153927 A1 | 8/2003 | DiPoto et al. | |
| 2003/0167058 A1 | 9/2003 | Shluzas | |
| 2003/0191371 A1 | 10/2003 | Smith et al. | |
| 2003/0195405 A1 | 10/2003 | Marino et al. | |
| 2003/0199871 A1 | 10/2003 | Foley et al. | |
| 2003/0236529 A1 | 12/2003 | Shluzas et al. | |
| 2004/0133201 A1 | 7/2004 | Shluzas et al. | |
| 2004/0230100 A1 | 11/2004 | Shluzas | |

FOREIGN PATENT DOCUMENTS

| | | |
|---|---|---|
| EP | 0807415 A2 | 11/1997 |
| EP | 0807415 A3 | 8/1998 |
| EP | 0980677 | 2/2000 |
| EP | 1305077 A1 | 5/2003 |
| JP | 2000083960 A2 | 3/2000 |
| JP | 2001149376 A2 | 6/2001 |
| WO | WO 92/21292 A2 | 12/1992 |
| WO | WO 93/14801 | 8/1993 |
| WO | WO 94/03114 | 2/1994 |
| WO | WO 95/10218 A1 | 4/1995 |
| WO | WO 95/32663 | 12/1995 |
| WO | WO 01/54560 A3 | 8/2001 |
| WO | WO 02/09801 A1 | 2/2002 |
| WO | WO 02/078767 A2 | 10/2002 |
| WO | WO 03/007783 A2 | 1/2003 |
| WO | 2004103188 | 12/2004 |
| WO | 2005032358 | 4/2005 |

OTHER PUBLICATIONS

U.S. Appl. No. 10/678,744, filed Oct. 2, 2003.
H. Boucher; "Method of Spinal Fusion"; *Clin Orthop* 1997; 335; pp. 4-9.
F. Magerl; "Stabilization of the Lower Thoracic Lumbar Spine With External Skeletal Fixation"; *Clin Orthop* 1984; 189; pp. 125-141.
Lisa A. Ferrara et al.; "A Biomechanical Comparison of Facet Screw Fixation and Pedicle Screw Fixation"; *Spine* vol. 28, No. 12; pp. 1226-1234.
Robert F. Heary et al.; "Circumferential Fusion for Spondylolisthesis in the Lumbar Spine"; *Neurosurg Focus* 13(1); 2002.

* cited by examiner

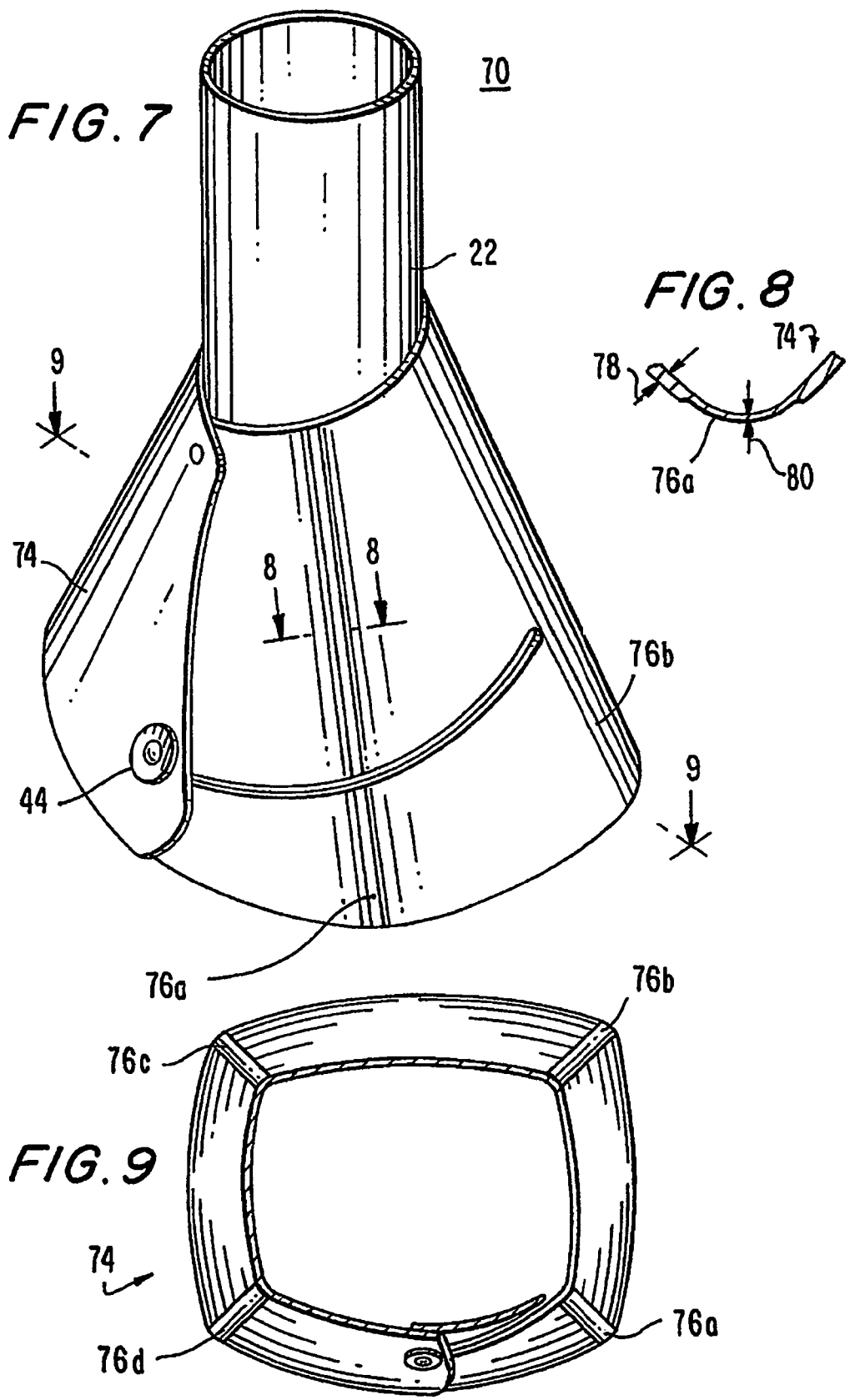

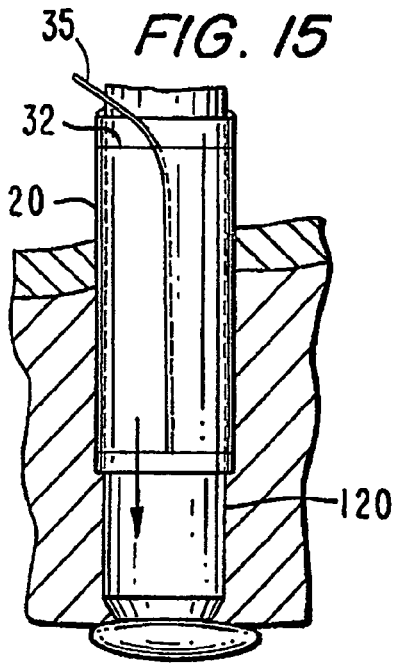
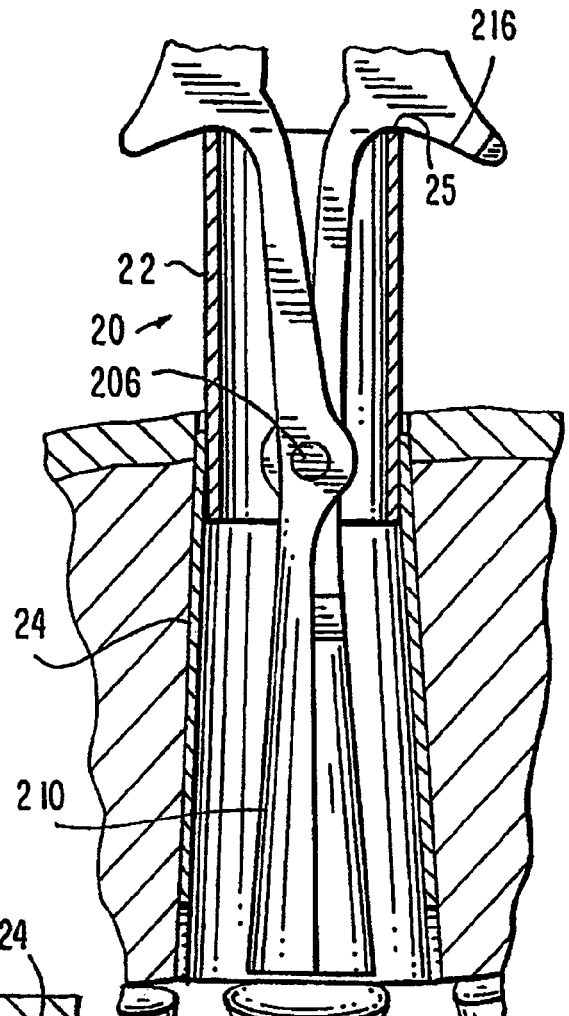
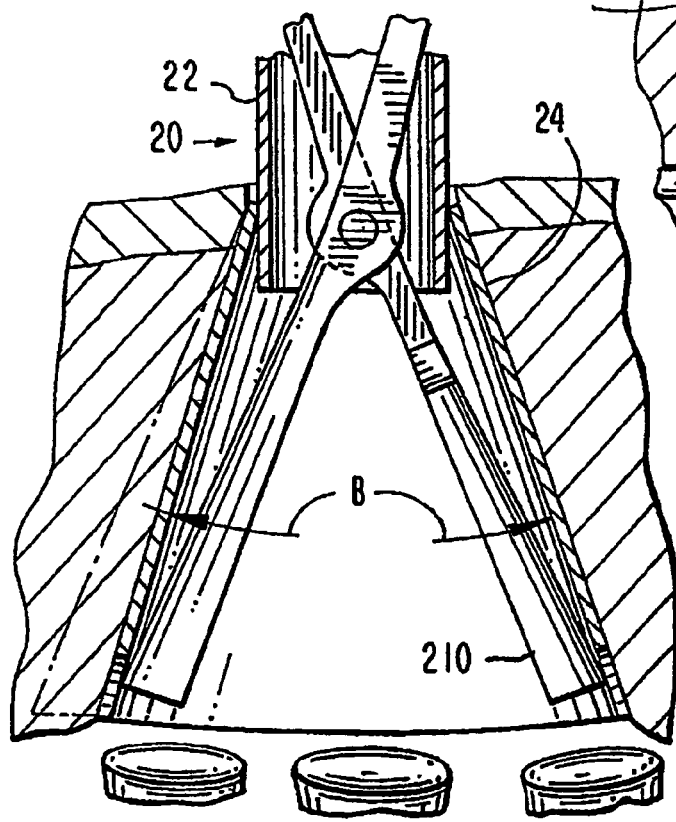

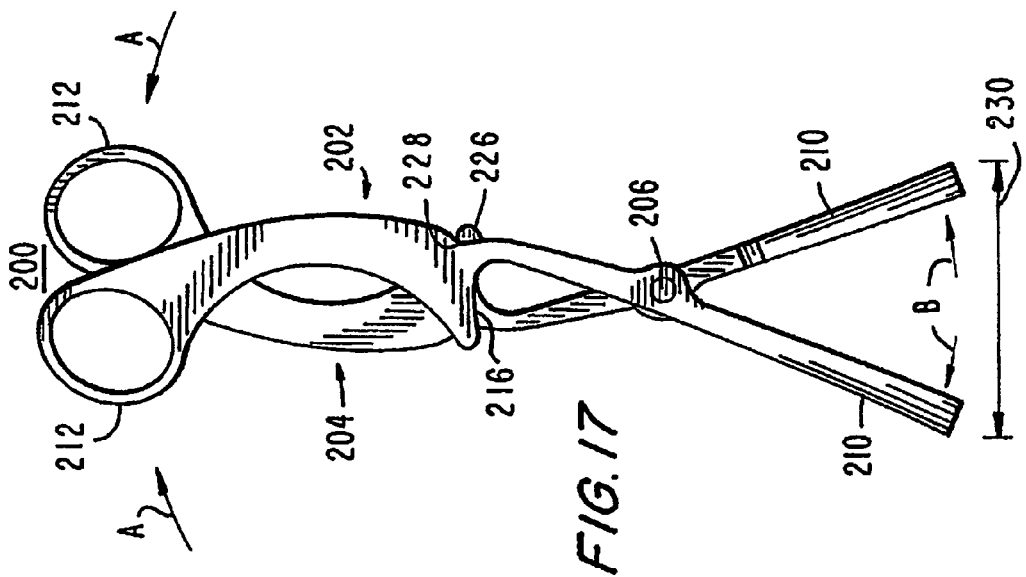
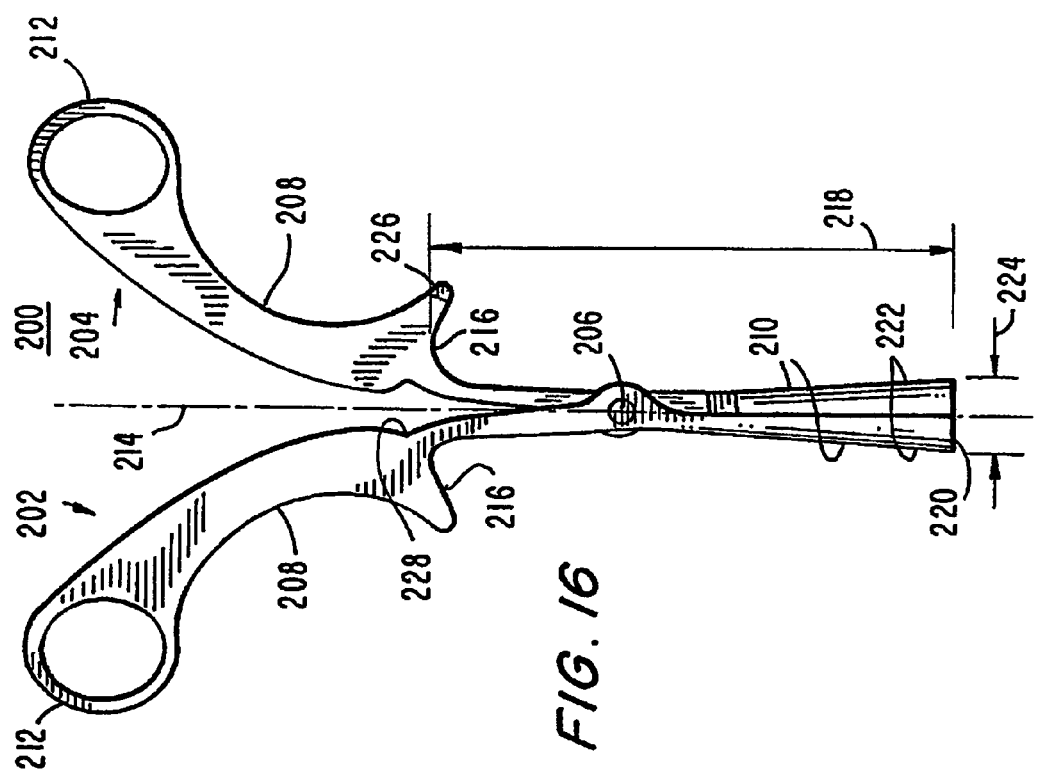

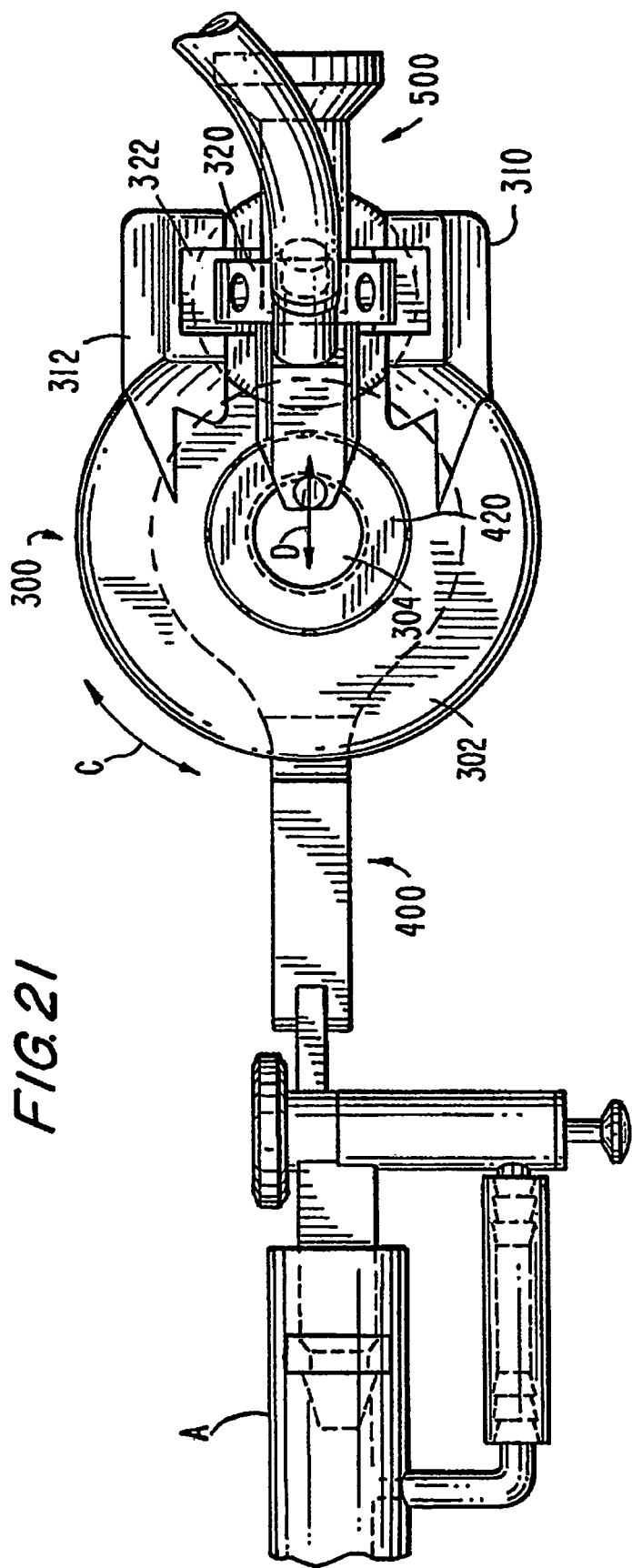

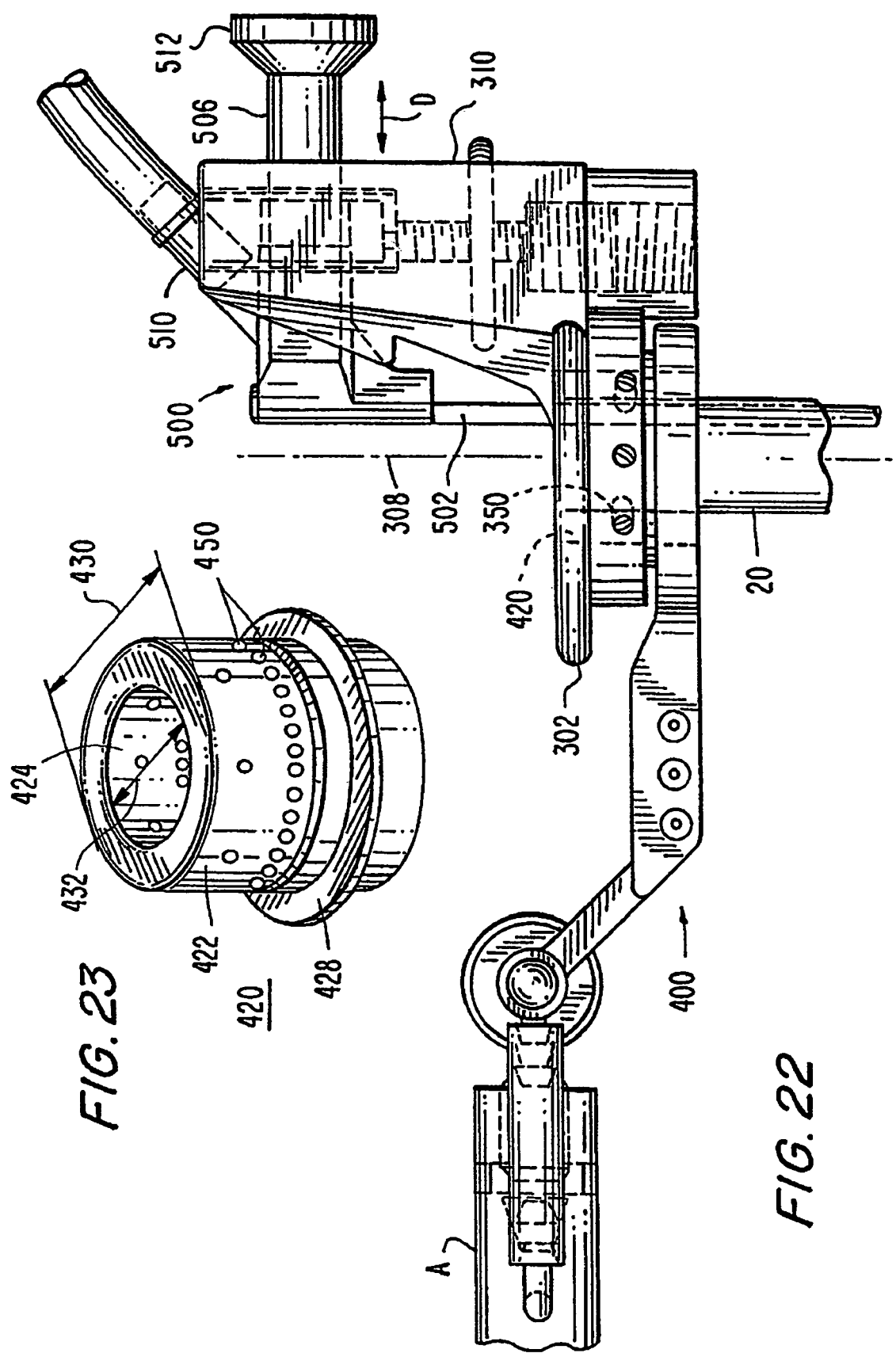

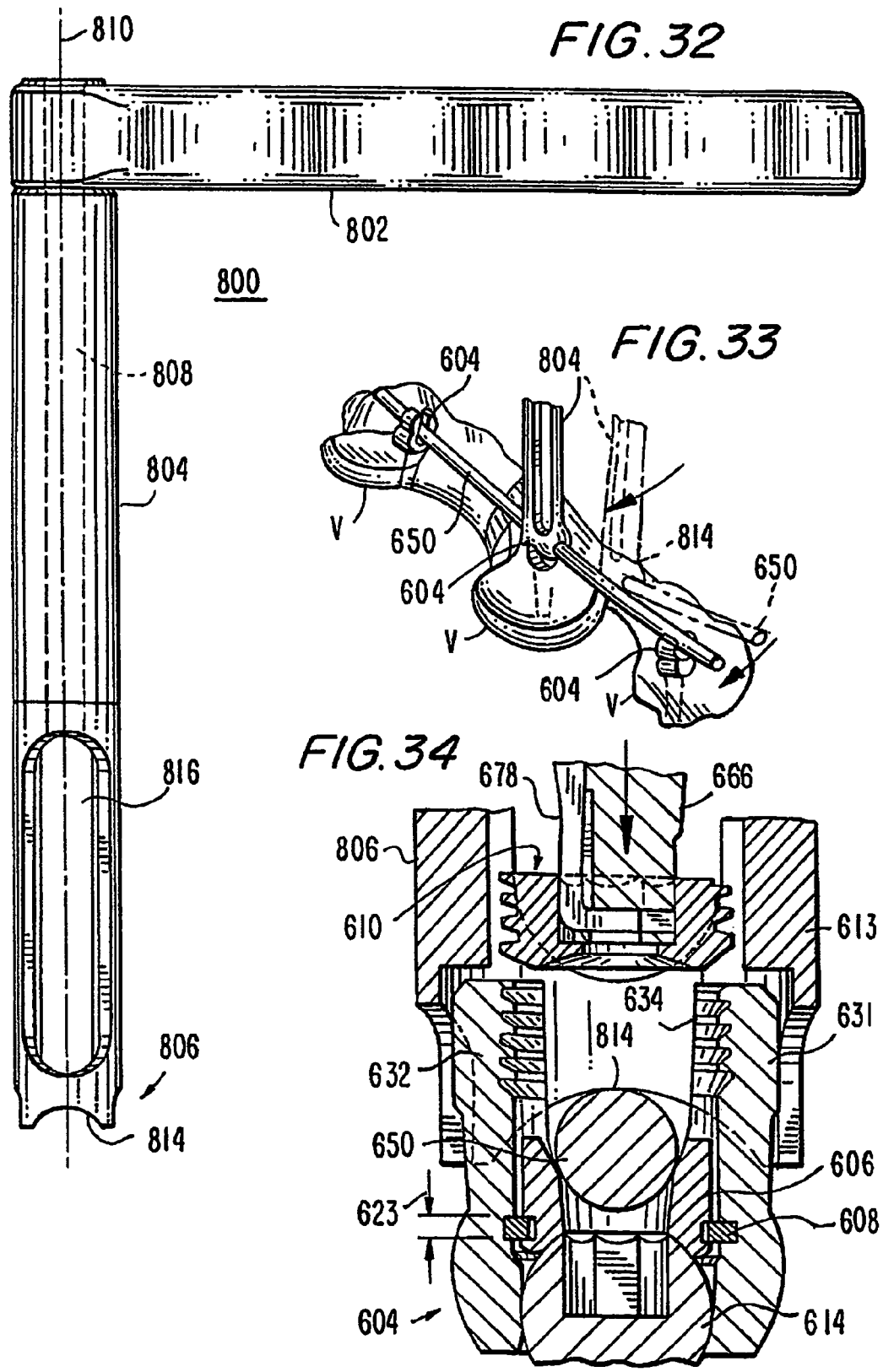

METHODS AND APPARATUSES FOR FIXATION OF THE SPINE THROUGH AN ACCESS DEVICE

BACKGROUND OF THE INVENTION

1. Field of the Invention

This application relates to methods of using access devices to perform minimally invasive surgery, such as procedures for stabilizing bone structures of a patient.

2. Description of the Related Art

Spinal surgery presents significant difficulties to the physician attempting to reduce chronic back pain or correct spinal deformities without introducing additional trauma due to the surgical procedure itself. In order to access the vertebrae to perform spinal procedures, the physician is typically required to make large incisions and cut or strip muscle tissue surrounding the spine. In addition, care must be taken not to injure nerve tissue in the area. Consequently, traditional surgical procedures of this type carry high risks of scarring, pain, significant blood loss, and extended recovery times.

Apparatuses for performing minimally invasive techniques have been proposed to reduce the trauma of posterior spinal surgery by reducing the size of the incision and the degree of muscle stripping in order to access the vertebrae. One such apparatus provides a constant diameter cannula, which is made narrow in order to provide a small entry profile. As a result, the cannula provides minimal space for the physician to observe the body structures and manipulate surgical instruments in order to perform the required procedures.

Once a doctor has exposed the vertebrae in some way, the most common treatment to reduce or eliminate degeneration of the spine or a portion thereof is fixation and/or fusion. Those conditions that compromise the spinal motion segments (adjacent vertebrae and the disc tissue or space in between) are often addressed by inserting a fusion device to promote bone growth between adjacent vertebrae. These devices are most commonly reinforced with a series of pedicle screws and rods to ensure minimal movement between adjacent vertebrae. These fixation devices provide load support for the spine, and can decrease the need for more extensive postoperative immobilization. Unfortunately, a narrow cannula is typically insufficient to perform one level spinal fixation procedures, which requires visualization of two vertebrae and introduction of screws, rods, as well as other large spinal fixation devices. Moreover, the pedicle screw fixation systems themselves require access to a larger area of the spine than the targeted disk area, increasing the trauma during surgery and increasing the time of patient recovery.

SUMMARY OF THE INVENTION

Accordingly, there is a need in the art for devices and methods for treating the spine which provide minimally invasive access to the spine such that fixation can be achieved with as little trauma to the surrounding area as possible.

One embodiment provides for a method to fix adjoining vertebrae of the spine of a patient. An access device is inserted into the patient at a surgical location adjacent the spine. This access device is inserted in a first configuration with a first cross-sectional area defined by its distal portion. Once at or near the surgical location, the access device is actuated to a second configuration having an enlarged cross-sectional area at its distal portion. With the access device in place, a fastener is delivered through the access device to the surgical location. The fastener is then advanced through a first vertebra and into a second vertebra. This fixation technique allows for the fixation of two adjacent vertebrae with minimal disruption and trauma to the surrounding tissue.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 7 is a perspective view of another embodiment of an expandable conduit in an enlarged configuration;

FIG. 8 is an enlarged sectional view of the expandable conduit of FIG. 7 taken along lines 8-8 of FIG. 7;

FIG. 9 is a sectional view of the expandable conduit of FIG. 7 taken along lines 9-9 of FIG. 7;

FIG. 15 is a sectional view illustrating one embodiment of a stage of one embodiment of a method for treating the spine of a patient;

FIG. 16 is a side view of one embodiment of an expander apparatus in a reduced profile configuration;

FIG. 17 is a side view of the expander apparatus of FIG. 16 in an expanded configuration;

FIG. 18 is a sectional view of the expander apparatus of FIGS. 16-17 inserted into the expandable conduit of FIG. 2, which has been inserted into a patient;

FIG. 19 is a sectional view of the expander apparatus of FIGS. 16-17 inserted into the expandable conduit of FIG. 2 and expanded to the expanded configuration to retract tissue;

FIG. 21 is a top view of the endoscope mount platform of FIG. 20 coupled with one embodiment of an indexing arm and one embodiment of an endoscope;

FIG. 22 is a side view of the endoscope mount platform of FIG. 20 illustrated with one embodiment of an indexing arm and one embodiment of an endoscope;

FIG. 23 is a perspective view of one embodiment of an indexing collar of the endoscope mount platform FIG. 20;

FIG. 27(a) is an enlarged side view of one embodiment of a biasing member illustrated in FIG. 27 taken from the perspective of the arrow 27a;

FIG. 32 is a side view of one embodiment of another surgical instrument;

FIG. 33 is a perspective view similar to FIG. 31 illustrating the apparatuses of FIGS. 26 and 32, in one embodiment of a stage of one embodiment of a method for treating the spine of a patient;

FIG. 34 is an enlarged sectional view of the apparatus of FIGS. 26 and 32, illustrating one embodiment of a stage of one embodiment of a method for treating the spine of a patient;

Figure 1:
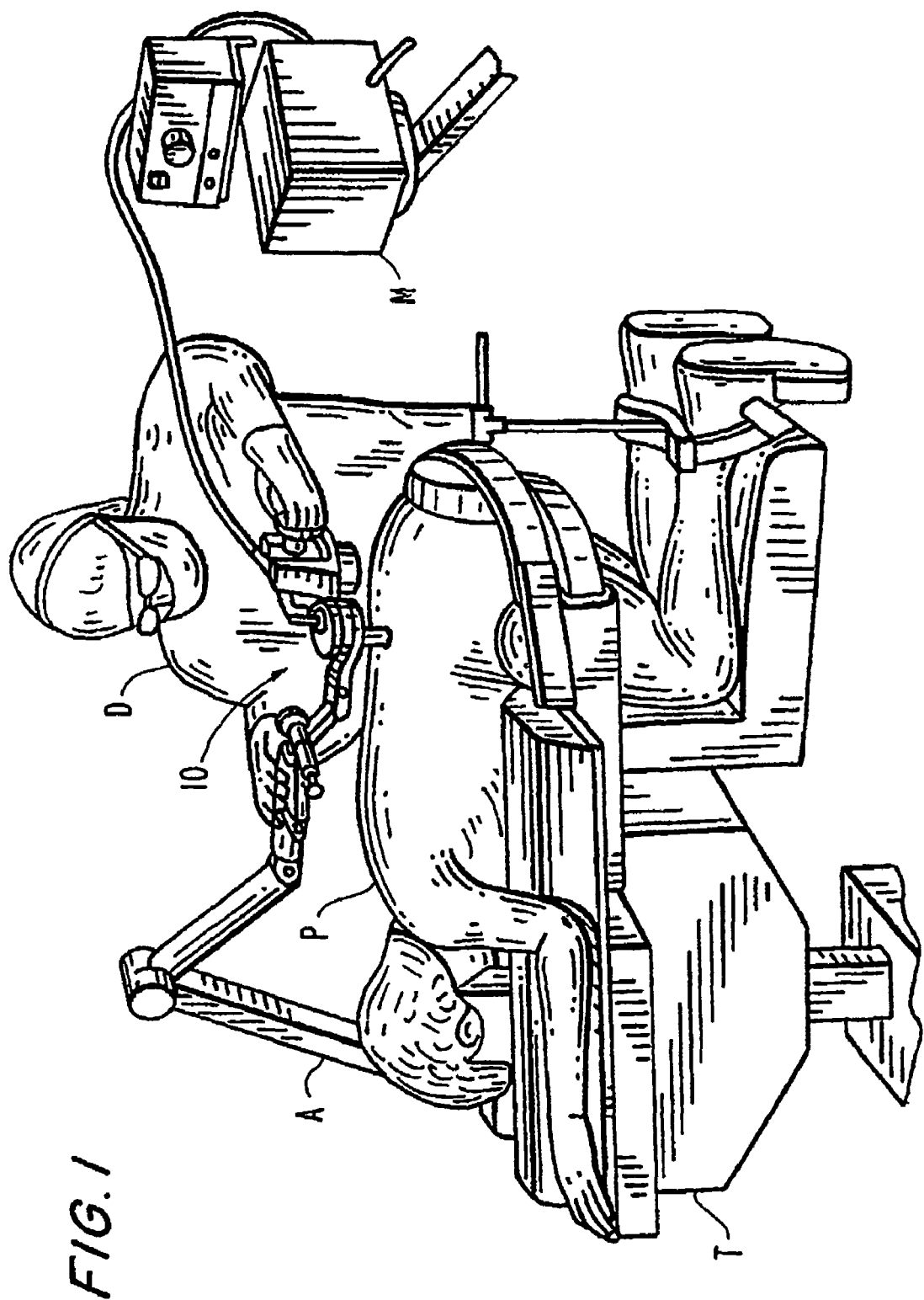
FIG. 1 is a perspective view of one embodiment of a surgical system and one embodiment of a method for treating the spine of a patient.
Figure 2:
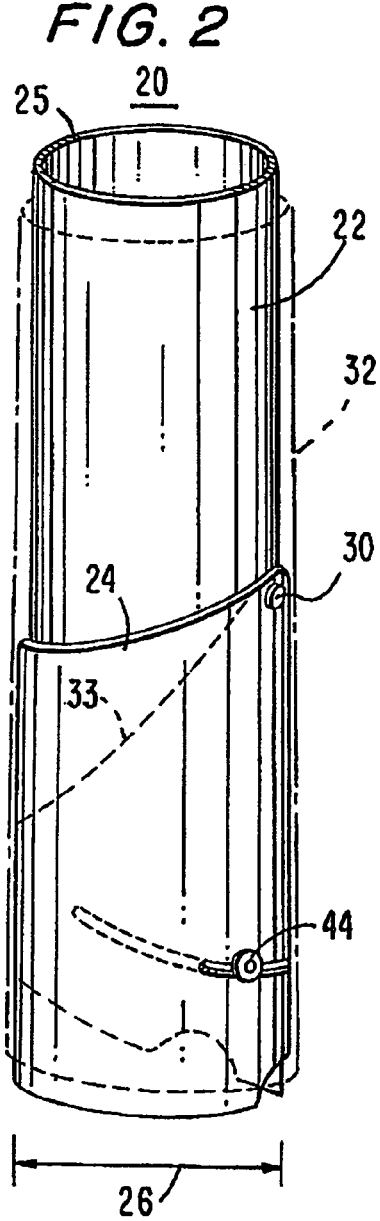
FIG. 2 is a perspective view of one embodiment of an expandable conduit in a reduced profile configuration.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENTS

As should be understood in view of the following detailed description, this application is directed to apparatuses and methods for treating the spine of a patient through an access device, also referred to herein as an expandable conduit. More particularly, the systems described below provide access to surgical locations at or near the spine and provide a variety of tools useful in performing treatment of the spine. Also, the systems described herein enable a surgeon to perform a wide variety of methods as described herein.

I. Systems for Performing Procedures at a Surgical Location

Various embodiments of apparatuses and procedures described herein will be discussed in terms minimally invasive procedures and apparatuses, e.g., of endoscopic apparatuses and procedures. However, many aspects of the present invention may find use in conventional, open, and mini-open procedures. In the drawings and description which follows, the term "proximal," as is traditional, refers to the end portion of the apparatus which is closest to the operator, while the term "distal" will refer to the end portion which is farthest from the operator.

FIG. 1 shows one embodiment of a surgical system 10 that can be used to perform a variety of methods or procedures. In at least a portion of the procedure, as discussed more fully below, the patient P typically is placed in the prone position on operating table T, taking care that the abdomen is not compressed and physiological lordosis is preserved, as is known in the art. The physician D is able to access the surgical site and perform the surgical procedure with the components of the system 10, which will be described in greater detail herein. The system 10 may be supported, in part, by a mechanical support arm A, such as the type generally disclosed in U.S. Pat. No. 4,863,133, which is hereby incorporated by reference herein in its entirety. One mechanical arm of this type is manufactured by Leonard Medical, Inc., 1464 Holcomb Road, Huntington Valley, Pa., 19006.

Visualization of the surgical site may be achieved in any suitable manner, e.g., by use of a viewing element, such as an endoscope, a camera, loupes, a microscope, direct visualization, or any other suitable viewing element, or a combination of the foregoing. In one embodiment, the viewing element provides a video signal representing images, such as images of the surgical site, to a monitor M. The viewing element may be an endoscope and camera which captures images to be displayed on the monitor M whereby the physician D is able to view the surgical site as the procedure is being performed. The endoscope and camera will be described in greater detail herein.

The systems and procedures will be described herein in connection with minimally invasive postero-lateral spinal surgery. One such method is a two level posterolateral fixation of the spine involving the L4, L5, and S1 vertebrae. (In the drawings, the vertebrae will generally be denoted by reference letter V.) The usefulness of the apparatuses and procedures is neither restricted to the postero-lateral approach nor to the L4, L5, and S1 vertebrae, but it may be used in other anatomical approaches and other vertebra(e) within the cervical, thoracic, and lumbar regions of the spine. The procedures may be directed toward surgery involving one or more vertebral levels. It is also useful for anterior and lateral procedures. Moreover, it is believed that the invention is also particularly useful where any body structures must be accessed beneath the skin and muscle tissue of the patient, and where it desirable to provide sufficient space and visibility in order to manipulate surgical instruments and treat the underlying body structures. For example, certain features or instrumentation described herein are particularly useful for a minimally invasive procedures, e.g., arthroscopic procedures. As discussed more fully below, one embodiment of an apparatus described herein provides an expandable conduit that has an expandable distal portion. The expandable distal portion prevents or substantially prevents the expandable conduit or instruments extended therethrough to the surgical site from being dislodging or popping out of the operative site.

The system 10 includes an expandable conduit or access device that provides a internal passage for surgical instruments to be inserted through the skin and muscle tissue of the patient P to the surgical site. The expandable conduit has a wall portion defining reduced profile configuration for initial percutaneous insertion into the patient. This wall portion may have any suitable arrangement. In one embodiment, discussed in more detail below, the wall portion has a generally tubular configuration that may be passed over a dilator that has been inserted into the patient to atraumatically enlarge an opening sufficiently large to receive the expandable conduit therein.

The wall portion of the expandable conduit is subsequently expanded to an enlarged configuration, by moving against the surrounding muscle tissue to at least partially define an enlarged surgical space in which the surgical procedures will be performed. In a sense, it acts as its own dilator. The expandable conduit may also be thought of as a retractor, and may be referred to herein as such. Typically, but not by way of limitation, the distal portion expands to a greater extent than the proximal portion, because the surgical procedures are to be performed at the surgical site which is adjacent the distal portion when the expandable conduit is inserted into the patient.

While in the reduced profile configuration, the expandable conduit defines a first unexpanded configuration. Thereafter, the expandable conduit enlarges the surgical space defined thereby by engaging the tissue surrounding the conduit and displacing the tissue radially outwardly as the conduit expands. The expandable conduit may be sufficiently rigid to displace such tissue during the expansion thereof. The expandable conduit may be resiliently biased to expand from the reduced profile configuration to the enlarged configuration. In addition, the conduit may also be manually expanded by an expander device with or without one or more surgical instruments inserted therein, as will be described below. The surgical site is at least partially defined by the expanded conduit itself. During expansion, the conduit moves from the first overlapping configuration to a second overlapping configuration.

In addition to enlargement, the distal end portion of the expandable conduit may be configured for relative movement with respect to the proximal end portion in order to allow the physician to precisely position the distal end portion at the desired location. This relative movement also provides the advantage that the proximal portion of the expandable conduit nearest the physician D may remain substantially stable during such distal movement. In an exemplary embodiment, the distal portion is a separate component which is pivotably or movably attached relative to the proximal portion. In another embodiment, the distal portion is flexible or resilient in order to permit such relative movement.

One embodiment of an expandable conduit is illustrated in FIGS. 2-6 and designated by reference number 20. The expandable conduit 20 includes a proximal wall portion 22, which has a tubular configuration, and a distal wall portion, which is an expandable skirt portion 24. The skirt portion 24 is enlargeable from a reduced profile configuration having an initial dimension 26 and corresponding cross-sectional area (illustrated in FIG. 2), to an enlarged configuration having a dimension 28 and corresponding cross-sectional area (illustrated in FIG. 4). In one embodiment, the skirt portion 24 is attached to the proximal wall portion 22 with a rivet 30, pin, or similar connecting device to permit movement of the skirt portion 24 relative to the proximal wall portion 22.

Figure 3:
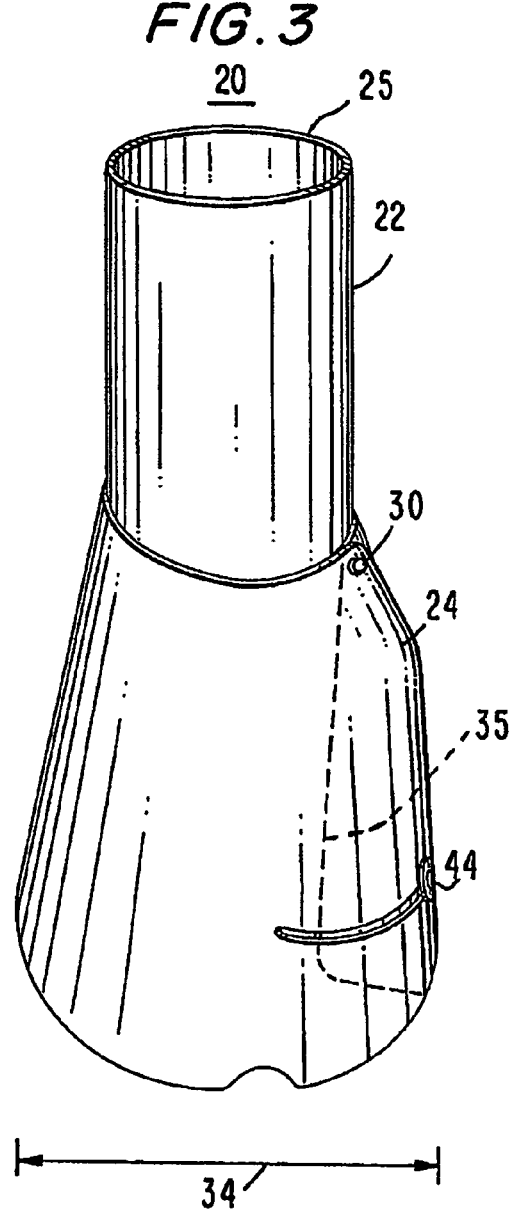
FIG. 3 is a perspective view of the expandable conduit of FIG. 2 in a first enlarged configuration.
Figure 4:
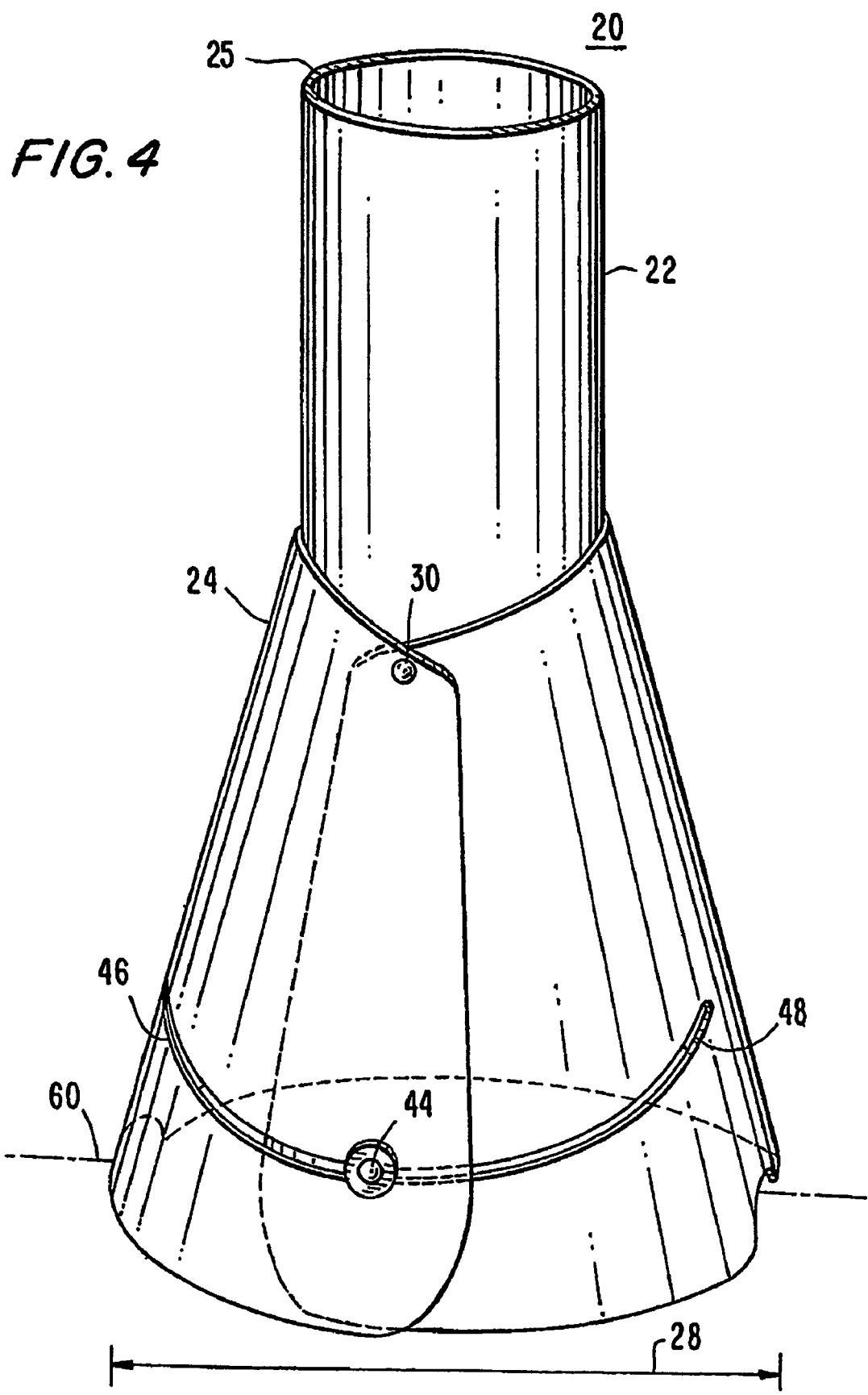
FIG. 4 is a perspective view of the expandable conduit of FIG. 2 in a second enlarged configuration.
Figure 6:
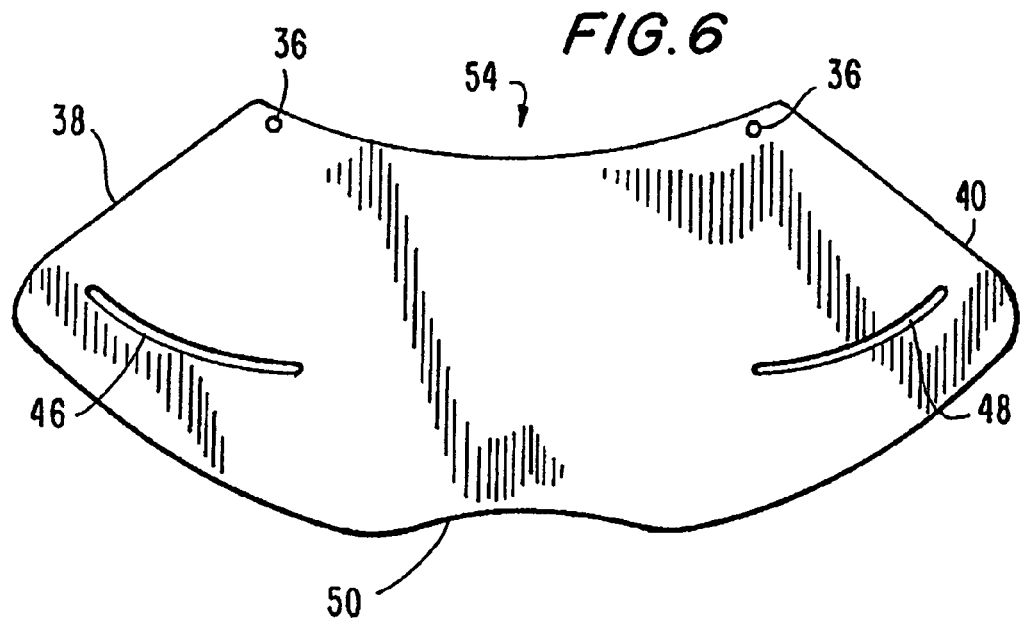
FIG. 6 is a view of another embodiment of a skirt portion of an expandable conduit.

In the illustrated embodiment, the skirt portion 24 is manufactured from a resilient material, such as stainless steel. The skirt portion 24 is manufactured so that it normally assumes an expanded configuration illustrated in FIG. 4. As illustrated in FIG. 3, the skirt portion 24 may assume an intermediate dimension 34 and corresponding cross-sectional area, which is greater than the dimension 26 of the reduced profile configuration of FIG. 2, and smaller than the dimension 28 of the enlarged configuration of FIG. 4. The skirt portion 24 may assume the intermediate configuration of FIG. 3 when deployed in the patient in response to the force of the tissue acting on the skirt portion 24. The intermediate dimension 34 will depend upon several factors, including the rigidity of the skirt portion 24, the surrounding tissue, and whether such surrounding tissue has relaxed or tightened during the course of the procedure. An outer plastic sleeve 32 (illustrated in dashed line in FIG. 2) may be provided which surrounds the expandable conduit 20 and maintains the skirt portion 24 in the reduced profile configuration. The outer sleeve 32 may have a braided polyester suture embedded within it (not shown), aligned substantially along the longitudinal axis thereof; such that when the suture is withdrawn, the outer sleeve 32 is torn, which allows the expandable conduit 20 to resiliently expand from the reduced profile configuration of FIG. 2 to the expanded configurations of FIGS. 3-4. While in the reduced profile configuration of FIG. 2, the skirt portion 24 defines a first overlapping configuration 33, as illustrated by the dashed line. As the skirt portion 24 resiliently expands, the skirt portion 24 assumes the expanded configuration, as illustrated in FIGS. 3-4.

The skirt portion 24 is sufficiently rigid that it is capable of displacing the tissue surrounding the skirt portion 24 as it expands. Depending upon the resistance exerted by surrounding tissue, the skirt portion is sufficiently rigid to provide some resistance against the tissue to remain in the configurations of FIGS. 3-4. Moreover, the expanded configuration of the skirt portion 24 is at least partially supported by the body tissue of the patient. The rigidity of the skirt portion 24 and the greater expansion at the distal portion creates a stable configuration that is at least temporarily stationary in the patient, which frees the physician from the need to actively support the conduit 20 until an endoscope mount platform 300 and a support arm 400 are subsequently added in one embodiment (see FIGS. 21-22).

Figure 5:
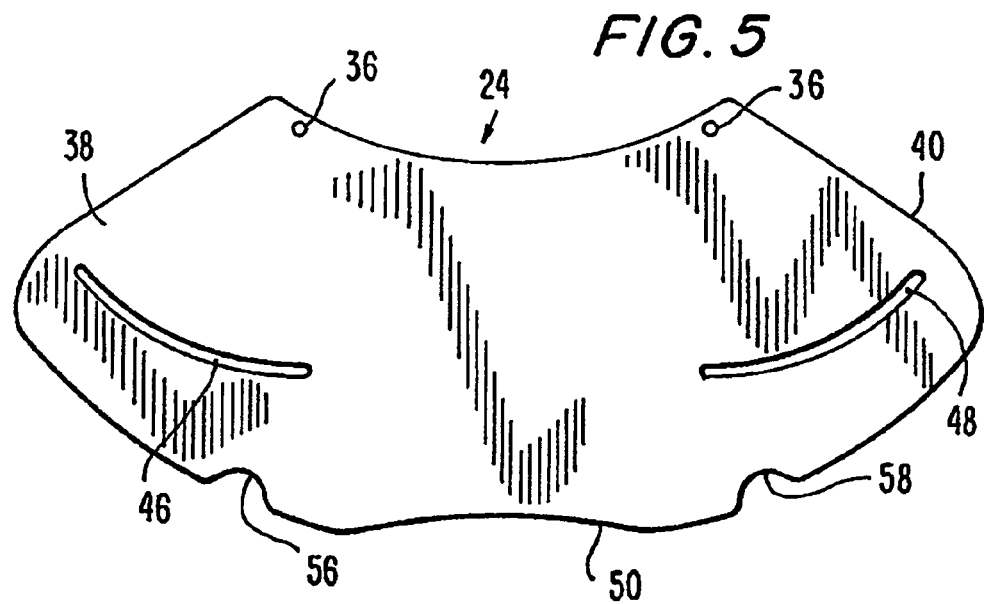
FIG. 5 is a view of one embodiment of a skirt portion of an expandable conduit.

The skirt portion 24 of the expandable conduit 20 is illustrated in an initial flattened configuration in FIG. 5. The skirt portion 24 may be manufactured from a sheet of stainless steel having a thickness of about 0.007 inches. In various embodiments, the dimension 28 of the skirt portion 24 is about equal to or greater than 50 mm, is about equal to or greater than 60 mm, is about equal to or greater than 70 mm, is about equal to or greater than 80 mm, or is any other suitable size, when the skirt portion 24 is in the enlarged configuration. In one embodiment, the dimension 28 is about 63 mm, when the skirt portion 24 is in the enlarged configuration. As discussed above, the unrestricted shape of the skirt portion 24 preferably is a circular or an oblong shape. The skirt portion 24 may also take on an oval shape, wherein the dimension 28 would define a longer dimension the skirt portion 24 and would be about 85 mm in one embodiment. In another embodiment, the skirt portion 24 has an oval shape and the dimension 28 defines a longer dimension of the skirt portion 24 and would be about 63 mm. An increased thickness, e.g., about 0.010 inches, may be used in connection with skirt portions having a larger diameter, such as about 65 mm. Other materials, such as nitinol or plastics having similar properties, may also be useful.

As discussed above, the skirt portion 24 is attached to the proximal wall portion 22 with a pivotable connection, such as rivet 30. A pair of rivet holes 36 are provided in the skirt portion 24 to receive the rivet 30. The skirt portion 24 also has two free ends 38 and 40 in one embodiment that are secured by a slidable connection, such as second rivet 44 (not shown in FIG. 5, illustrated in FIGS. 2-4). A pair of complementary slots 46 and 48 are defined in the skirt portion 24 adjacent the free ends 38 and 40. The rivet 44 is permitted to move freely within the slots 46 and 48. This slot and rivet configuration allows the skirt portion 24 to move between the reduced profile configuration of FIG. 2 and the enlarged or expanded configurations of FIGS. 3-4. The use of a pair of slots 46 and 48 reduces the risk of the "button-holing" of the rivet 44, e.g., a situation in which the opening of the slot becomes distorted and enlarged such that the rivet may slide out of the slot, and cause failure of the device. However, the likelihood of such occurrence is reduced in skirt portion 24 because each of the slots 46 and 48 in the double slot configuration has a relatively shorter length than a single slot configuration. Being shorter, the slots 46, 48 are less likely to be distorted to the extent that a rivet may slide out of position. In addition, the configuration of rivet 44 and slots 46 and 48 permits a smoother operation of enlarging and reducing the skirt portion 24, and allows the skirt portion 24 to expand to span as many as three vertebrae, e.g., L4, L5, and S1, to perform multi-level fixation alone or in combination with a variety of other procedures, as discussed below.

An additional feature of the skirt portion 24 is the provision of a shallow concave profile 50 defined along the distal edge of the skirt portion 24, which allows for improved placement of the skirt portion 24 with respect to the body structures and the surgical instruments defined herein. In one embodiment, a pair of small scalloped or notched portions 56 and 58, are provided, as illustrated in FIG. 5. When the skirt portion 24 is assembled, the notched portions 56 and 58 are oriented in the cephcaudal direction (indicated by an arrow 60 in FIG. 4) and permit instrumentation, such as an elongated member 650 used in a fixation procedure (described in detail below), to extend beyond the area enclosed by the skirt portion 24 without moving or raising the skirt portion 24 from its location to allow the elongated member 650 to pass under the skirt portion 24. The notched portions 56, 58 are optional, as illustrated in connection with another embodiment of an expandable conduit 54, illustrated in FIG. 6, and may be eliminated where the physician deems the notches to be unnecessary for the procedures to be performed (e.g., where fixation does not require extended access, as discussed more fully below.)

As illustrated in FIG. 4, the skirt portion 24 may be expanded to a substantially conical configuration having a substantially circular or elliptical profile. In another embodiment, features may be provided on the skirt portion which facilitate the bending of the skirt portion at several locations to provide a pre-formed enlarged configuration. For example, another embodiment of an expandable conduit 70, illustrated in FIGS. 7-9, provides a skirt portion 74 that has four sections 76a, 76b, 76c, 76d having a reduced thickness. For a skirt portion 74 having a thickness 78 of about 0.007 inches, reduced thickness sections 76a, 76b, 76c, 76d may have a thickness 80 of about 0.002-0.004 inches (FIG. 8). The reduced thickness sections 76a, 76b, 76c, 76d may have a width 82 of about 1-5 mm. The thickness 78 of the skirt portion 74 may be reduced by milling or grinding, as is known in the art. When the skirt portion 74 is opened, it moves toward a substantially rectangular configuration, as shown in FIG. 9, subject to the resisting forces of the body tissue. In another embodiment (not shown), a skirt portion may be provided with two reduced thickness sections (rather than the four reduced thickness sections of skirt 74) which would produce a substantially "football"-shaped access area.

Figure 10:
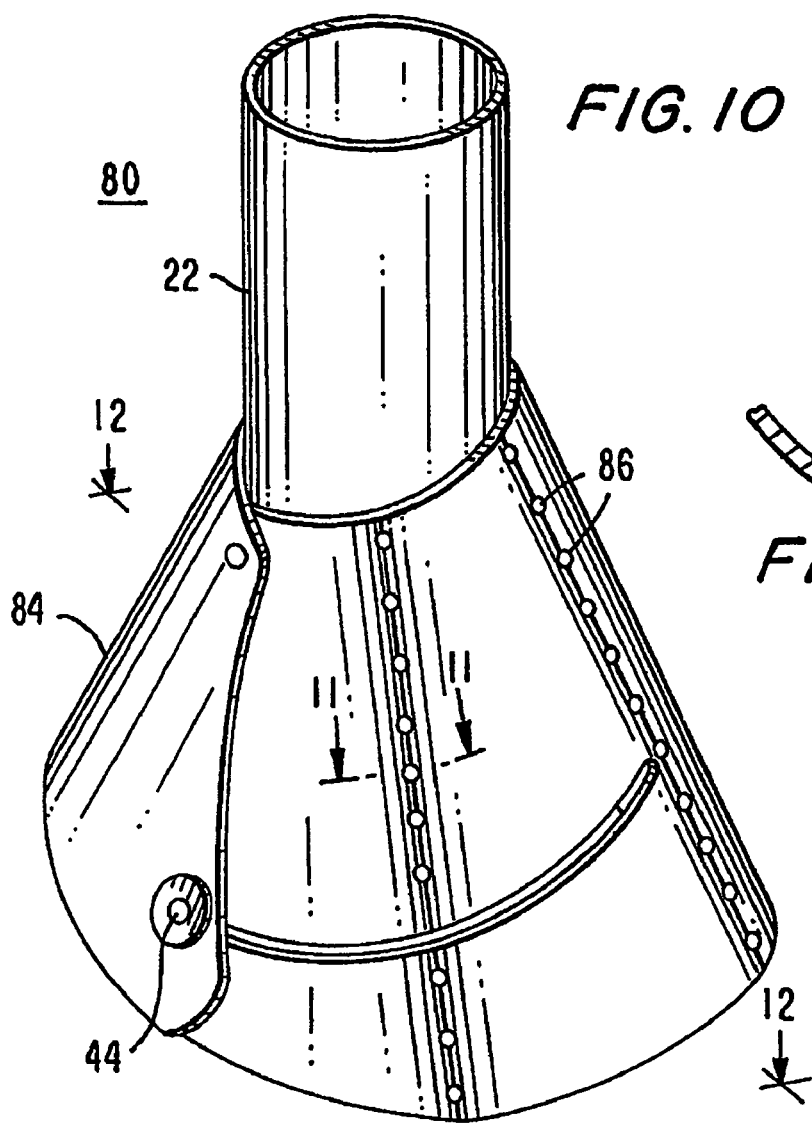
FIG. 10 is a perspective view of another embodiment of an expandable conduit in an enlarged configuration.
Figure 11:
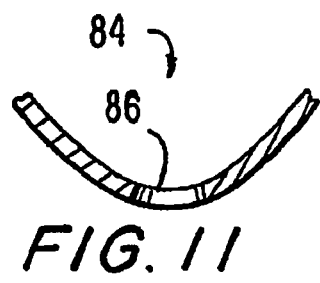
FIG. 11 is an enlarged sectional view of the expandable conduit of FIG. 10 taken along lines 11-11 of FIG. 10.
Figure 12:
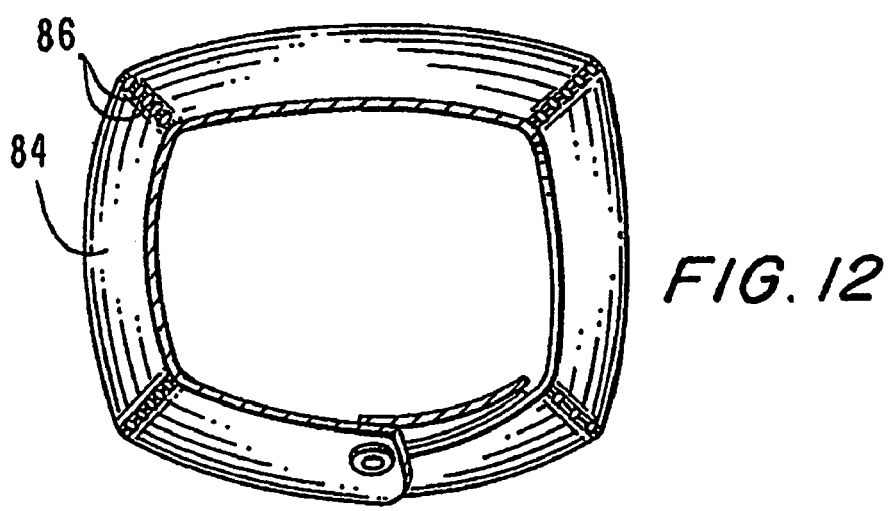
FIG. 12 is a sectional view of the expandable conduit of FIG. 10 taken along lines 12-12 of FIG. 10.

FIGS. 10-12 show another embodiment of an expandable conduit 80. The expandable conduit 80 has a skirt portion 84 with a plurality of perforations 86. The perforations 86 advantageously increase the flexibility at selected locations. The size and number of perforations 86 may vary depending upon the desired flexibility and durability. In another embodiment, the skirt portion 84 may be scored or otherwise provided with a groove or rib in order to facilitate the bending of the skirt portion at the desired location.

Figure 13:
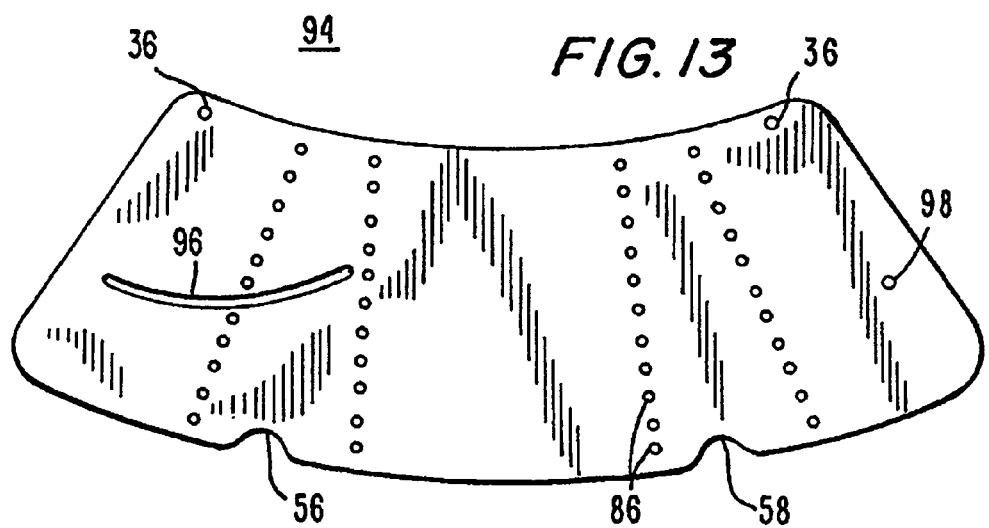
FIG. 13 is a view of a portion of another embodiment of the expandable conduit.
Figure 14:
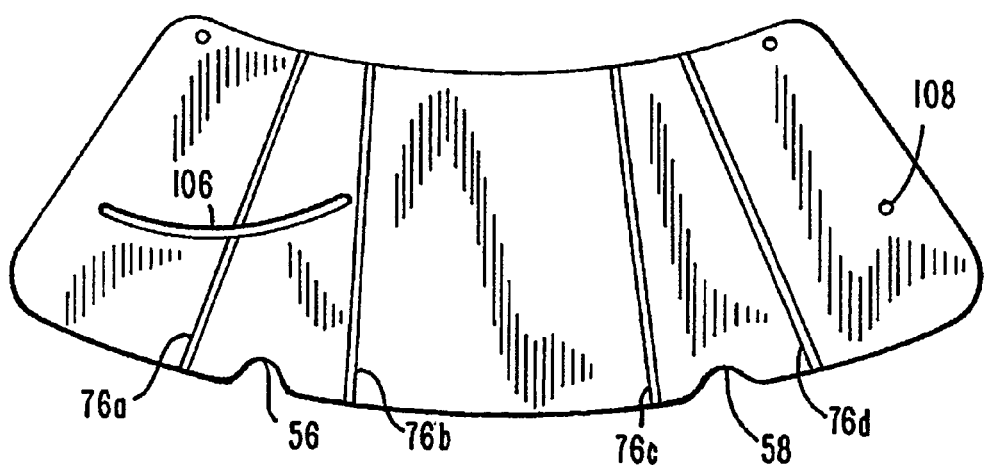
FIG. 14 is a view of a portion of another embodiment of the expandable conduit.
Figure 20:
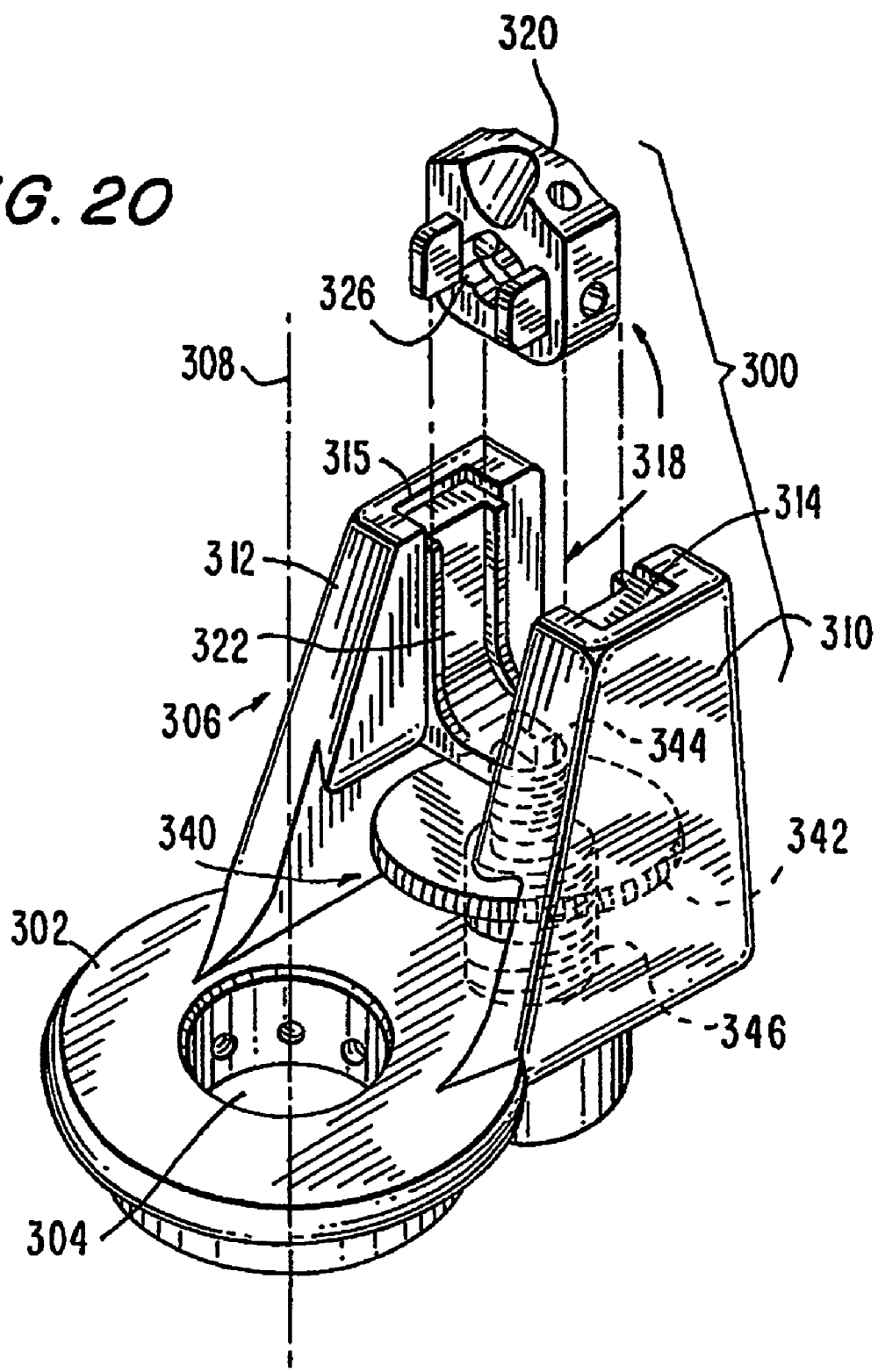
FIG. 20 is an exploded perspective view of one embodiment of an endoscope mount platform.

FIG. 13 illustrates another embodiment of an expandable conduit that has a skirt portion 94 having one slot 96 and an aperture 98. A rivet (not shown) is stationary with respect to the aperture 98 and slides within the slot 96. FIG. 14 illustrates another embodiment of an expandable conduit that has a skirt portion 104 that includes an aperture 108. The apertures 108 receives a rivet (not shown) that slides within elongated slot 106.

Further details of the expandable conduit are described in U.S. Pat. No. 6,187,00, and in U.S. patent application Ser. No. 09/772,605, filed Jan. 30, 2001, U.S. application Ser. No. 10/361,887 filed Feb. 10, 2003, and application Ser. No. 10/280,489 filed Oct. 25, 2002, which are incorporated by reference in their entirety herein.

In one embodiment of a procedure, an early stage involves determining a point in the skin of the patient at which to insert the expandable conduit. The access point preferably corresponds to the posterior-lateral aspects of the spine. Manual palpation and Anterior-Posterior (AP) fluoroscopy may be used to determine preferred or optimal locations for forming an incision in the skin of the patient. In one embodiment, the expandable conduit 20 preferably is placed midway (in the cephcaudal direction) between the L4 through S1 vertebrae, centrally about 4-7 cm from the midline of the spine.

After the above-described location is determined, an incision is made at the location. A guide wire (not shown) is introduced under fluoroscopic guidance through the skin, fascia, and muscle to the approximate surgical site. A series of dilators is used to sequentially expand the incision to the desired width, about 23 mm in one procedure, without damaging the structure of surrounding tissue and muscles. A first dilator is placed over the guide wire, which expands the opening. The guide wire is then subsequently removed. A second dilator that is slightly larger than the first dilator is placed over the first dilator, which expands the opening further. Once the second dilator is in place, the first dilator is subsequently removed. This process of (1) introducing a next-larger-sized dilator coaxially over the previous dilator and (2) subsequently removing the previous dilator when the next-larger-sized dilator is in place continues until an opening of the desired size is created in the skin, muscle, and subcutaneous tissue. In one embodiment of the method, desired opening size is about 23 mm. (Other dimensions of the opening, e.g., about 20 mm, 27 mm, 30 mm, etc., are also useful with this apparatus in connection with spinal surgery, and still other dimensions are contemplated.)

FIG. 15 shows that following placement of a dilator 120, which is the largest dilator in the above-described dilation process, the expandable conduit 20 is introduced in its reduced profile configuration and positioned in a surrounding relationship over the dilator 120. The dilator 120 is subsequently removed from the patient, and the expandable conduit 20 is allowed to remain in position.

Once positioned in the patient, the expandable conduit 20 may be enlarged to provide a passage for the insertion of various surgical instruments and to provide an enlarged space for performing the procedures described herein. As described above, the expandable conduit may achieve the enlargement in several ways. In one embodiment, a distal portion of the conduit may be enlarged, and a proximal portion may maintain a constant diameter. The relative lengths of the proximal portion 22 and the skirt portion 24 may be adjusted to vary the overall expansion of the conduit 20. Alternatively, such expansion may extend along the entire length of the expandable conduit 20. In one embodiment of a procedure, the expandable conduit 20 may be expanded by removing a suture 35 and tearing the outer sleeve 32 surrounding the expandable conduit 20, and subsequently allowing the skirt portion 24 to resiliently expand towards its fully expanded configuration as (illustrated in FIG. 4) to create an enlarged surgical space from the L4 to the S1 vertebrae. The resisting force exerted on the skirt portion 24 may result in the skirt portion 24 assuming the intermediate configuration illustrated in FIG. 3. Under many circumstances, the space created by the skirt portion 24 in the intermediate configuration is a sufficiently large working space to perform the procedure described herein. Once the skirt portion 24 has expanded, the rigidity and resilient characteristics of the skirt portion 24 allow the expandable conduit 20 to resist closing to the reduced profile configuration of FIG. 2 and to at least temporarily resist being expelled from the incision. These characteristics create a stable configuration for the conduit 20 to remain in position in the body, supported by the surrounding tissue. It is understood that additional support may be needed, especially if an endoscope is added.

According to one embodiment of a procedures, the expandable conduit 20 may be further enlarged at the skirt portion 24 using an expander apparatus to create a surgical access space. An expander apparatus useful for enlarging the expandable conduit has a reduced profile configuration and an enlarged configuration. The expander apparatus is inserted into the expandable conduit in the reduced profile configuration, and subsequently expanded to the enlarged configuration. The expansion of the expander apparatus also causes the expandable conduit to be expanded to the enlarged configuration. In some embodiments, the expander apparatus may increase the diameter of the expandable conduit along substantially its entire length in a conical configuration. In other embodiments, the expander apparatus expands only a distal portion of the expandable conduit, allowing a proximal portion to maintain a constant diameter.

In addition to expanding the expandable conduit, the expander apparatus may also be used to position the distal portion of the expandable conduit at the desired location for the surgical procedure. The expander engages an interior wall of the expandable conduit, and moves the conduit to the proper location. For the embodiments in which the distal portion of the expandable conduit is relatively movable with respect to the proximal portion, the expander apparatus is useful to position the distal portion without substantially disturbing the proximal portion.

In some procedures, an expander apparatus is used to further expand the skirt portion 24 towards the enlarged configuration (illustrated in FIG. 4). The expander apparatus is inserted into the expandable conduit, and typically has two or more members which are movable to engage the interior wall of the skirt portion 24 and apply a force sufficient to further expand the skirt portion 24. FIGS. 16 and 17 show one embodiment of an expander apparatus 200 that has a first component 202 and a second component 204. a first component 202 and a second component 204 of the expander apparatus 200 are arranged in a tongs-like configuration and are pivotable about a pin 206. The first and second components 202 and 204 are typically constructed of steel having a thickness of about 9.7 mm. Each of the first and second components 202 and 204 has a proximal handle portion 208 and a distal expander portion 210. Each proximal handle portion 208 has a finger grip 212 that may extend transversely from an axis, e.g., a longitudinal axis 214, of the apparatus 200. The proximal handle portion 208 may further include a stop element, such as flange 216, that extends transversely from the longitudinal axis 214. The flange 216 is dimensioned to engage the proximal end 25 of the expandable conduit 20 when the apparatus 200 is inserted a predetermined depth. This arrangement provides a visual and tactile indication of the proper depth for inserting the expander apparatus 200. In one embodiment, a dimension 218 from the flange 216 to the distal tip 220 is about 106 mm. The dimension 218 is determined by the typical depth of the body structures beneath the skin surface at which the surgical procedure is being performed. The distal portions 210 are each provided with an outer surface 222 for engaging the inside wall of the skirt portion 24. The outer surface 222 is a frusto-conical surface in one embodiment. The expander apparatus 200 has an unexpanded distal width 224 at the distal tip 220 that is about 18.5 mm in one embodiment.

In use, the finger grips 212 are approximated towards one another, as indicated by an arrow A in FIG. 17, which causes the distal portions 210 to move to the enlarged configuration, as indicated by arrows B. The components 202 and 204 are also provided with a cooperating tab 226 and shoulder portion 228 which are configured for mutual engagement when the distal portions 210 are in the expanded configuration. In the illustrated embodiment, the expander apparatus 200 has an expanded distal width 230 that extends between the distal portions 210. The expanded distal width 230 can be about 65 mm or less, about as large as 83 mm or less, or any other suitable width. The tab 226 and shoulder portion 228 together limit the expansion of the expander apparatus 200 to prevent expansion of the skirt portion 24 of the expandable conduit 20 beyond its designed dimension, and to minimize trauma to the underlying tissue. Further details of the expander apparatus are described in U.S. patent application Ser. No. 09/906,463 filed Jul. 16, 2001, which is incorporated by reference in their entirety herein.

When the expandable conduit 20 is inserted into the patient and the outer sleeve 32 is removed, the skirt portion 24 expands to a point where the outward resilient expansion of the skirt portion 24 is balanced by the force of the surrounding tissue. The surgical space defined by the conduit may be sufficient to perform any of a number of surgical procedures or combination of surgical procedures described herein. However, if it is desired to expand the expandable conduit 20 further, the expander apparatus 200 may be inserted into the expandable conduit 20 in the reduced profile configuration until the shoulder portions 216 are in approximation with the proximal end 25 of the skirt portion 24 of the expandable conduit 20, as shown in FIG. 18.

FIG. 18 shows the expander apparatus 200 is inserted in the expandable conduit 20 in the reduced profiled configuration. Expansion of the expander apparatus 200 is achieved by approximating the handle portions 212 (not shown in FIG. 18), which causes the distal portions 210 of the expander apparatus 200 to move to a spaced apart configuration. As the distal portions 210 move apart and contact the inner wall of the skirt portion 24, the skirt portion 24 is expanded by allowing the rivet 44 to slide within the slots 46 and 48 of the skirt portion 24. When the distal portions 210 reach the maximum expansion of the skirt portion 24 (illustrated by a dashed line in FIG. 19), the tab 226 and shoulder portion 228 of the expander apparatus 200 come into engagement to prevent further expansion of the tong portions (as illustrated in FIG. 17). The conduit 20 may be alternatively further expanded with a balloon or similar device.

A subsequent, optional step in the procedure is to adjust the location of the distal portion of the expandable conduit 20 relative to the body structures to be operated on. For example, the expander apparatus 200 may also be used to engage the inner wall of the skirt portion 24 of the expandable conduit 20 in order to move the skirt portion 24 of the expandable conduit 20 to the desired location. For an embodiment in which the skirt portion 24 of the expandable conduit 20 is relatively movable relative to the proximal portion, e.g. by use of the rivet 30, the expander apparatus 200 is useful to position the skirt portion 24 without substantially disturbing the proximal portion 22 or the tissues closer to the skin surface of the patient. As will be described below, the ability to move the distal end portion, e.g., the skirt portion 24, without disturbing the proximal portion is especially beneficial when an additional apparatus is mounted relative to the proximal portion of the expandable conduit, as described below.

An endoscope mount platform 300 and indexing arm 400 provide securement of an endoscope 500 on the proximal end 25 of the expandable conduit 20 for remotely viewing the surgical procedure, as illustrated in FIGS. 20-23. The endoscope mount platform 300 may also provide several other functions during the surgical procedure. The endoscope mount platform 300 includes a base 302 that extends laterally from a central opening 304 in a general ring-shaped configuration. The base 302 provides an aid for the physician, who is primarily viewing the procedure by observing a monitor, when inserting surgical instruments into the central opening 304. For example, the size of the base 302 provides visual assistance (as it may be observable in the physician's peripheral vision) as well as provides tactile feedback as the instruments are lowered towards the central opening 304 and into the expandable conduit 20.

The endoscope mount platform 300 further provides a guide portion 306 that extends substantially parallel to a longitudinal axis 308 away from the central opening 304. The base 302 is typically molded as one piece with the guide portion 306. The base 302 and guide portion 306 may be constructed as a suitable polymer such as polyetheretherketone (PEEK).

The guide portion 306 includes a first upright member 310 that extends upward from the base 302 and a second upright member 312 that extends upward from the base 302. The upright members 310, 312 each have a respective vertical grooves 314 and 315 that can slidably receive an endoscopic mount assembly 318.

The endoscope 500 (not shown in FIG. 20) is movably mounted to the endoscope mount platform 300 by the endoscope mount assembly 318. The endoscope mount assembly 318 includes an endoscope mount 320 and a saddle unit 322. The saddle unit 322 is slidably mounted within the grooves 314 and 315 in the upright members 310 and 312. The endoscope mount 320 receives the endoscope 500 through a bore 326 which passes through the endoscope mount 320. Part of the endoscope 500 may extend through the expandable conduit 20 substantially parallel to longitudinal axis 308 into the patient's body 130.

The endoscope mount 320 is removably positioned in a recess 328 defined in the substantially "U"-shaped saddle unit 322, which is selectively movable in a direction parallel to the longitudinal axis 308 in order to position the endoscope 500 at the desired height within the expandable conduit 20 to provide a zoom feature to physician's view of the surgical procedure.

A screw mechanism 340 is positioned on the base 302 between the upright members 310 and 312, and is used to selectively move the saddle unit 322, and the endoscope mount 320 and the endoscope 500 which are supported by the saddle unit 322. The screw mechanism 340 comprises a thumb wheel 342 and a spindle 344. The thumb wheel 343 is rotatably mounted in a bore in the base 302. The thumb wheel 342 has an external thread 346 received in a cooperating thread in the base 302. The spindle 344 is mounted for movement substantially parallel to the central axis 308. The spindle 344 has a first end received in a rectangular opening in the saddle unit 322, which inhibits rotational movement of the spindle 344. The second end of the spindle 344 has an external thread which cooperates with an internal thread formed in a bore within the thumb wheel 342. Rotation of the thumb wheel 342 relative to the spindle 344, causes relative axial movement of the spindle unit 344 along with the saddle unit 322. Further details of the endoscope mount platform are described in U.S. patent application Ser. No. 09/491,808 filed Jan. 28, 2000, application Ser. No. 09/821,297 filed Mar. 29, 2001, and application Ser. No. 09/940,402 filed Aug. 27, 2001.

FIG. 21-23 show that the endoscope mount platform 300 is mountable to the support arm 400 in one embodiment. The support arm 400, in turn, preferably is mountable to mechanical support, such as mechanical support arm A, discussed above in connection with FIG. 1. The support arm 400 rests on the proximal end 25 of the expandable conduit 20. The support arm 400 includes an indexing collar 420, which is received in the central opening 304 of the base 302 of endoscope mount platform 300. The indexing collar 420 is substantially toroidal in section and has an outer peripheral wall surface 422, an inner wall surface 424, and a wall thickness 426 that is the distance between the wall surfaces 422, 424. The indexing collar 420 further includes a flange 428, which supports the indexing collar 420 on the support arm 400.

The collars 420 advantageously make the surgical system 10 a modular in that different expandable conduits 20 may be used with a single endoscope mount platform 300. For example, expandable conduits 20 of different dimensions may be supported by providing of indexing collars 420 to accommodate each conduit size while using a single endoscope mount platform 300. The central opening 304 of the endoscope mount platform 300 has constant dimension, e.g., a diameter of about 32.6 mm. An appropriate indexing collar 420 is selected, e.g., one that is appropriately sized to support a selected expandable conduit 20. Thus the outer wall 422 and the outer diameter 430 are unchanged between different indexing collars 420, although the inner wall 424 and the inner diameter 432 vary to accommodate differently sized conduits 20.

The indexing collar 420 is mounted to the proximal portion of the expandable conduit 20 and allows angular movement of the endoscope mount platform 300 with respect thereto about the longitudinal axis 308 (as indicated by an arrow C in FIG. 21). The outer wall 422 of the index collar 420 includes a plurality of hemispherical recesses 450 that can receive one or more ball plungers 350 on the endoscope mount platform 300 (indicated in dashed line.) This arrangement permits the endoscope mount platform 300, along with the endoscope 500, to be fixed in a plurality of discrete angular positions. Further details of the support arm and indexing collar are described in U.S. Pat. No. 6,361,488, issued Mar. 26, 2002, U.S. Pat. No. 6,530,880 issued Mar. 11, 2003, and application Ser. No. 09/940,402 filed Aug. 27, 2001.

Figure 24:
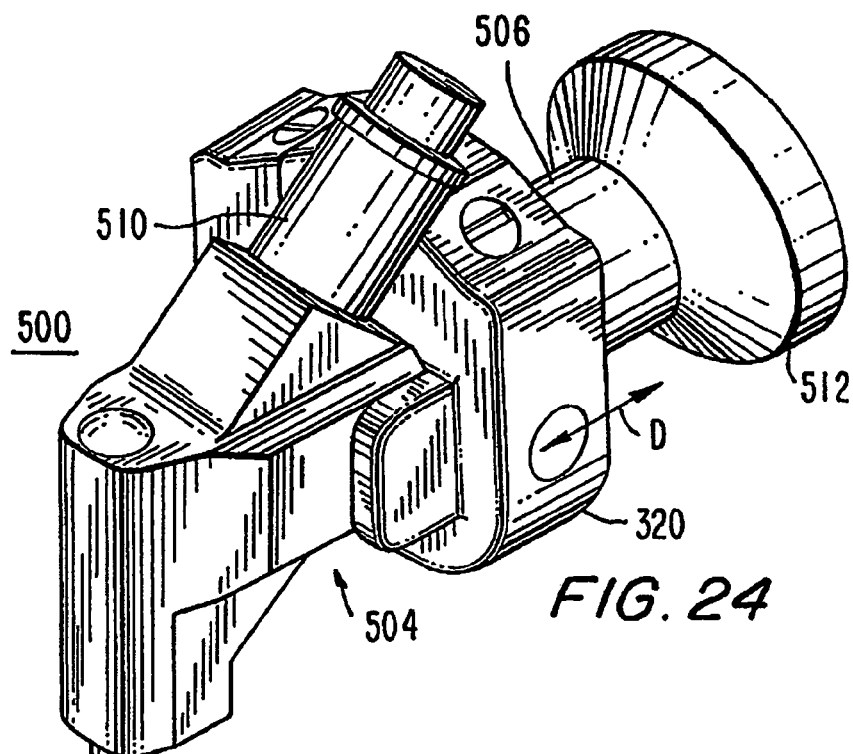
FIG. 24 is a perspective view of one embodiment of an endoscope.

FIG. 24 shows one embodiment of the endoscope 500, which has an elongated configuration that extends into the expandable conduit 20 in order to view the surgical site. In particular, the endoscope 500 has an elongated rod portion 502 and a body portion 504 which is substantially perpendicular thereto. In the illustrated embodiment, the rod portion 502 of endoscope 500 has a diameter of about 4 mm and a length of about 106 mm. Body portion 504 may define a tubular portion 506 which is configured to be slidably received in the bore 326 of endoscope mount 320 as indicated by an arrow D. The slidable mounting of the endoscope 500 on the endoscope mount platform 300 permits the endoscope 500 to adjust to configurations that incorporate different conduit diameters. Additional mobility of the endoscope 500 in viewing the surgical site may be provided by rotating the endoscope mount platform 300 about the central axis 308 (as indicated by arrow C in FIG. 21).

The rod portion 502 supports an optical portion (not shown) at a distal end 508 thereof, which may define a field of view of about 105 degrees and a direction of view 511 of about 25-30 degrees. An eyepiece 512 is positioned at an end portion of the body portion 504. A camera (not shown) preferably is attached to the endoscope 500 adjacent the eyepiece 512 with a standard coupler unit. A light post 510 supplies illumination to the surgical site at the distal end portion 508. A preferred camera for use in the system and procedures described herein is a three chip unit that provides greater resolution to the viewed image than a single chip device.

Figure 25:
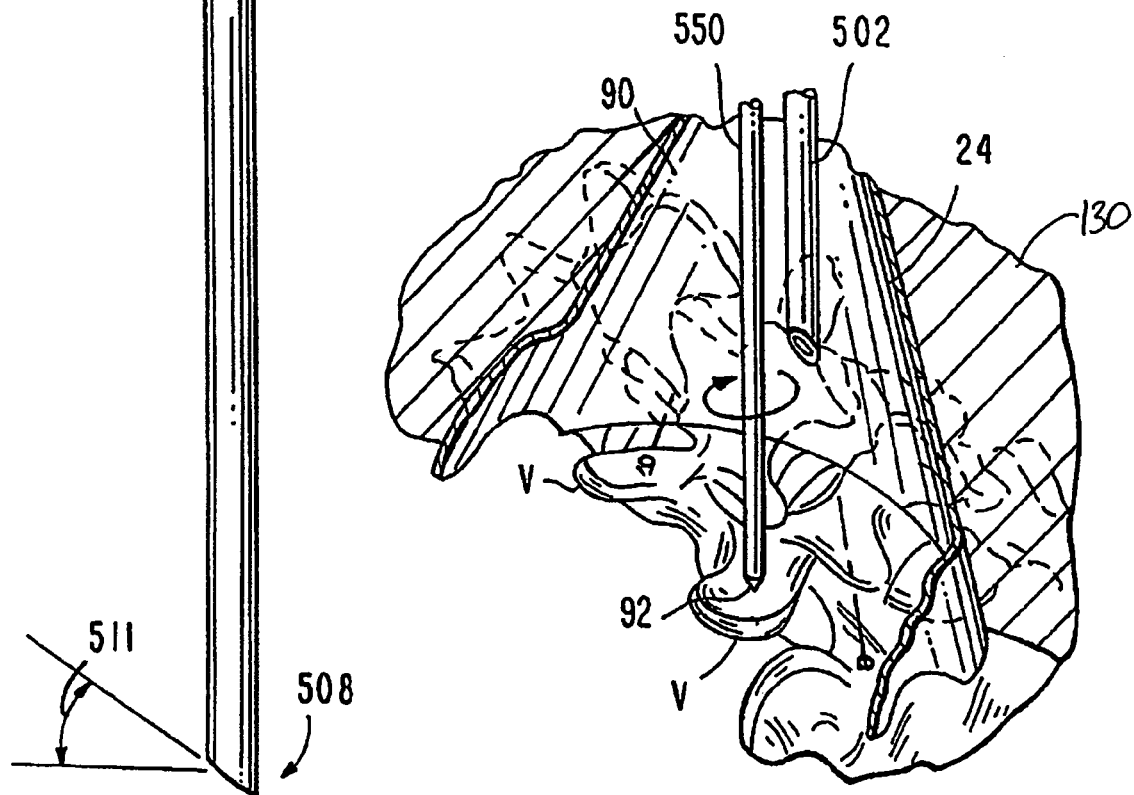
FIG. 25 is a partial sectional view of one embodiment of a stage of one embodiment of a method for treating the spine of a patient.

A subsequent stage in the procedure involves placing the support arm 400 and the endoscope mount platform 300 on the proximal portion, e.g., the proximal end 25, of the expandable conduit 20 (FIGS. 1 and 22), and mounting of the endoscope 500 on the endoscope mount platform 300. A next step is insertion of one or more surgical instruments into the expandable conduit 20 to perform the surgical procedure on the body structures at least partially within the operative space defined by the expanded portion of the expandable conduit. FIG. 25 shows that in one method, the skirt portion 24 of expandable conduit 20 at least partially defines a surgical site or operative space 90 in which the surgical procedures described herein may be performed. Depending upon the overlap of the skirt portion, the skirt portion may define a surface which is continuous about the circumference or which is discontinuous having one or more gaps where the material of the skirt portion does not overlap.

One procedure performable through the expandable conduit 20, described in greater detail below, is a two-level spinal fixation. Surgical instruments inserted into the expandable conduit may be used for debridement and decortication. In particular, the soft tissue, such as fat and muscle, covering the vertebrae may be removed in order to allow the physician to visually identify the various "landmarks," or vertebral structures, which enable the physician to locate the location for attaching a fastener, such a fastener 600, discussed below, or other procedures, as will be described herein. Allowing visual identification of the vertebral structures enables the physician to perform the procedure while viewing the surgical area through the endoscope, microscope, loupes, etc., or in a conventional, open manner.

Tissue debridement and decortication of bone are completed using one or more debrider blades, bipolar sheath, high speed burr, and additional conventional manual instruments. The debrider blades are used to excise, remove and aspirate the soft tissue. The bipolar sheath is used to achieve hemostasis through spot and bulk tissue coagulation. The debrider blades and bipolar sheath are described in greater detail in U.S. Pat. No. 6,193,715, assigned to Medical Scientific, Inc., which is incorporated by reference in its entirety herein. The high speed burr and conventional manual instruments are also used to continue to expose the structure of the vertebrae.

A subsequent stage is the attachment of fasteners to the vertebrae V. Prior to attachment of the fasteners, the location of the fastener attachment is confirmed. In the exemplary embodiment, the pedicle entry point of the L5 vertebrae is located using visual landmarks as well as lateral and A/P fluoroscopy, as is known in the art. With continued reference to FIG. 25, the entry point 92 is prepared with an awl 550. The pedicle hole 92 is completed using instruments known in the art such as a straight bone probe, a tap, and a sounder. The sounder, as is known in the art, determines whether the hole that is made is surrounded by bone on all sides, and that there has been no perforation of the pedicle wall.

After hole in the pedicle is provided at the entry point 92 (or at any point during the procedure), an optional step is to adjust the location of the distal portion of the expandable conduit 20. This may be performed by inserting the expander apparatus 200 into the expandable conduit 20, expanding the distal portions 210, and contacting the inner wall of the skirt portion 24 to move the skirt portion 24 to the desired location. This step may be performed while the endoscope 500 is positioned within the expandable conduit 20, and without substantially disturbing the location of the proximal portion of the expandable conduit 20 to which the endoscope mount platform 300 may be attached.

Figure 26:
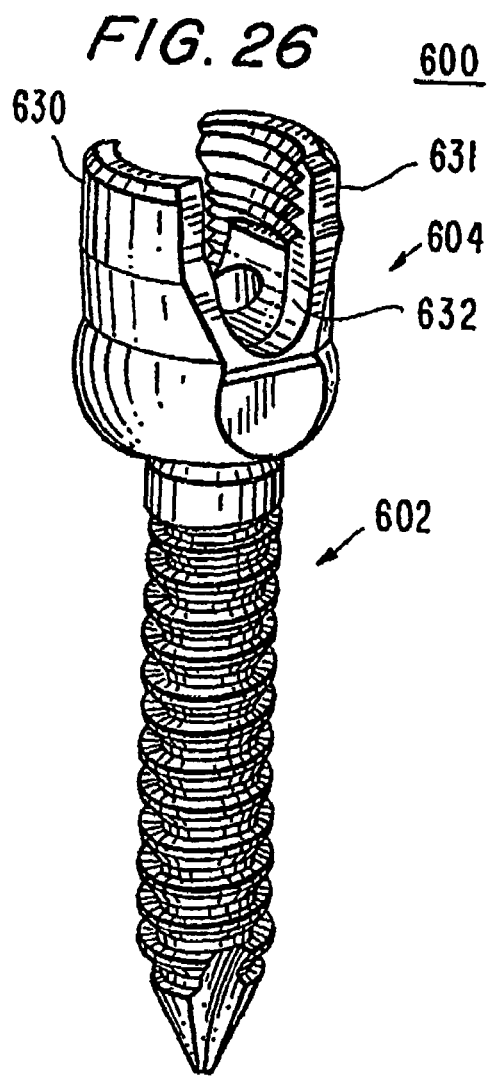
FIG. 26 is a perspective view of one embodiment of a fastener.
Figure 27A:
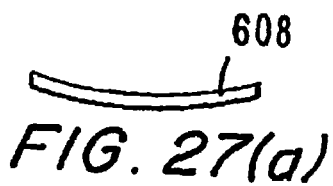
Figure 27:
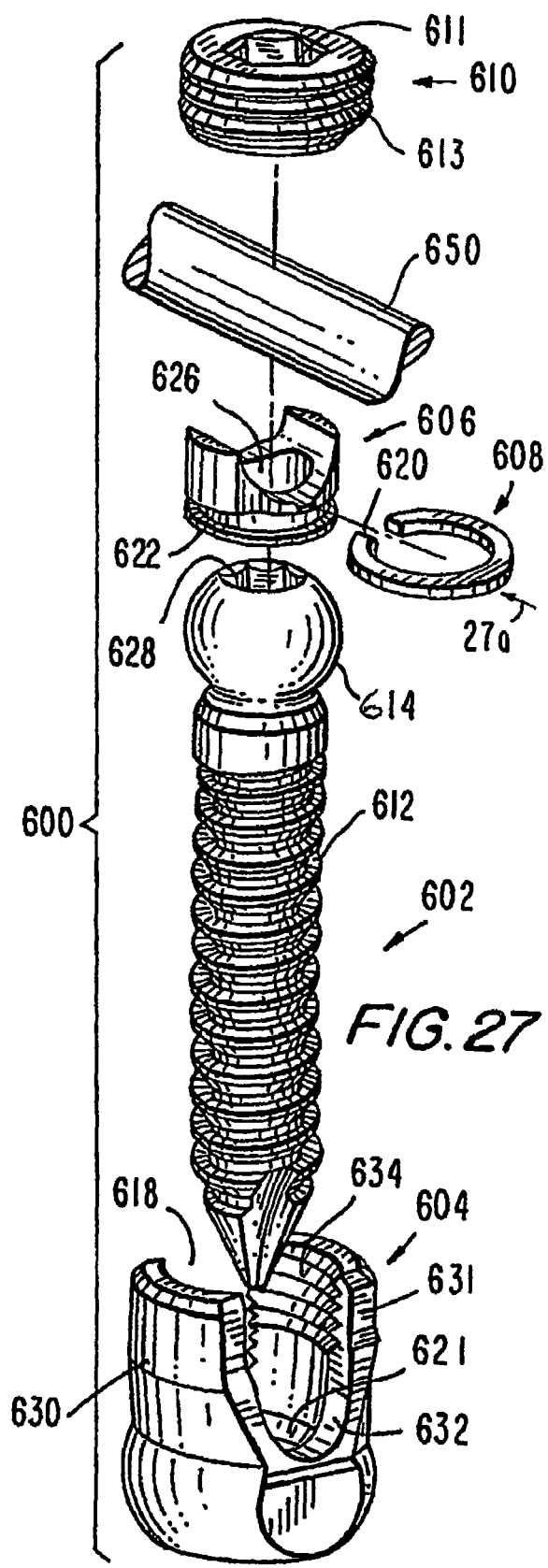
FIG. 27 is an exploded perspective view of the fastener of FIG. 26.

FIGS. 26-27 illustrate a fastener 600 that is particularly applicable in a procedures involving fixation. The fastener 600 is described in greater detail in U.S. patent application Ser. No. 10/075,668, filed Feb. 13, 2002 and application Ser. No. 10/087,489, filed Mar. 1, 2002, which are incorporated by reference in their entirety herein. Fastener 600 includes a screw portion 602, a housing 604, a spacer member 606, a biasing member 608, and a clamping member, such as a cap screw 610. The screw portion 602 has a distal threaded portion 612 and a proximal, substantially spherical joint portion 614. The threaded portion 612 is inserted into the hole 92 in the vertebrae, as will be described below. The substantially spherical joint portion 614 is received in a substantially annular, part spherical recess 616 in the housing 604 in a ball and socket joint relationship (see also FIG. 29).

As illustrated in FIG. 27, the fastener 600 is assembled by inserting the screw portion 602 into a bore in a passage 618 in the housing 604, until the joint portion 614 engages the annular recess 616. The screw portion 602 is retained in the housing 604 by the spacer member 606 and biasing member 608. The biasing member 608 provides a biasing force to drive the spacer member 606 in frictional engagement with the joint portion 614 of the screw member 602 and the annular recess 616 of the housing 604. The biasing provided by the biasing member 602 frictionally maintains the relative positions of the housing 604 with respect to the screw portion 602. The biasing member 608 is selected such that biasing force prevents unrestricted movement of the housing 604 relative to the screw portion 602. However, the biasing force is insufficient to resist the application of force by a physician to move the housing 604 relative to the screw portion 602. In other words, this biasing force is strong enough maintain the housing 604 stationary relative to the screw portion 602, but this force may be overcome by the physician to reorient the housing 604 with respect to the screw member 602, as will be described below.

In the illustrated embodiment, the biasing member 608 is a resilient ring having a gap 620, which permits the biasing member 608 to radially contract and expand. FIG. 27(*a*) illustrates that the biasing member 608 may have an arched shape, when viewed end-on. The arched shape of the spring member 608 provides the biasing force, as will be described below. The spacer member 606 and the biasing member 608 are inserted into the housing 604 by radially compressing the biasing member into an annular groove 622 in the spacer member 606. The spacer member 606 and the biasing member 608 are slid into the passage 618 until the distal surface of the spacer member 606 engages the joint portion 614 of the screw portion 602, and the biasing member 608 expands radially into the annular groove 622 in the housing 604. The annular groove 622 in the housing 604 has a dimension 623 which is smaller than the uncompressed height of the arched shape of the biasing member 608. When the biasing member 608 is inserted in the annular groove 620, the biasing member 608 is flattened against its normal bias, thereby exerting the biasing force to the spacer member 606. It is understood that similar biasing members, such as coiled springs, belleville washers, or the like may be used to supply the biasing force described herein.

The spacer member 606 is provided with a longitudinal bore 626, which provides access to a hexagonal recess 628 in the proximal end of the joint portion 614 of the screw member 602. The proximal portion of the housing 604 includes a pair of upright members 630 and 631 that are separated by substantially "U"-shaped grooves 632. A recess for receiving elongated member 650 is defined by the pair of grooves 632 between upright member 630 and 631. Elongated member 650 to be placed distally into the housing 604 in an orientation substantially transverse to the longitudinal axis of the housing 604, as will be described below. The inner walls of he upright members 630 and 631 are provided with threads 634 for attachment of the cap screw 610 by threads 613 therein.

Figure 28:
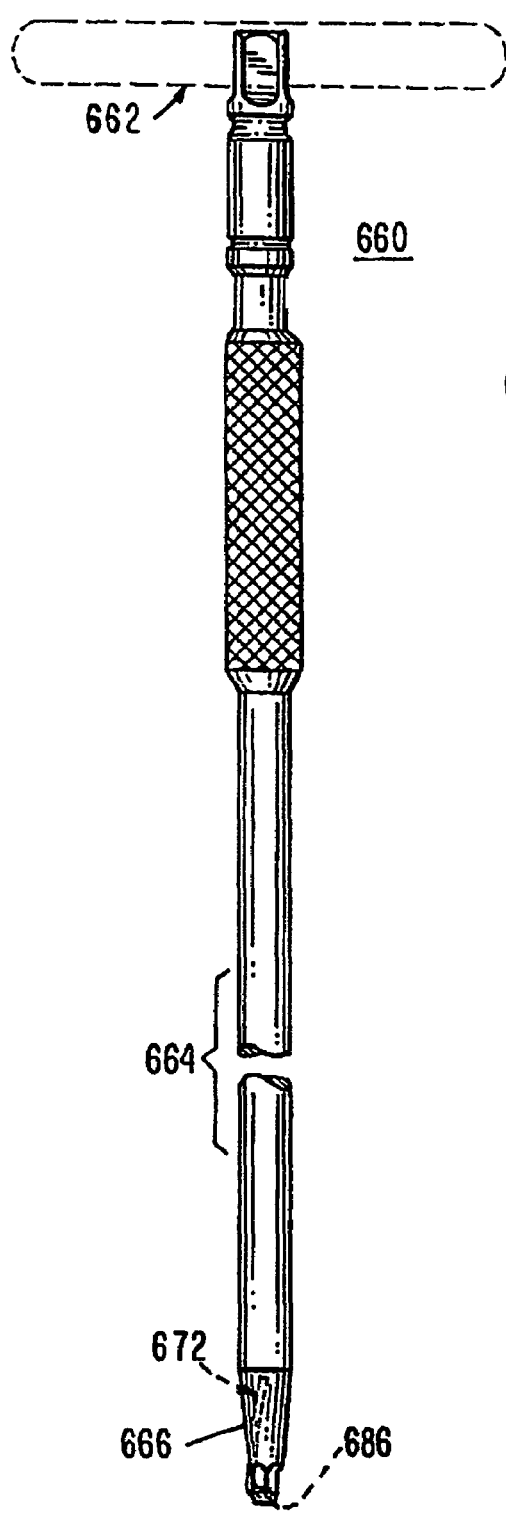
FIG. 28 is a perspective view of one embodiment of a surgical instrument.

The fastener 600 is inserted into the expandable conduit 20 and guided to the prepared hole 92 in the vertebrae as a further stage of the procedure. The fastener 600 must be simultaneously supported and rotated in order to be secured in hole 92. In the illustrated embodiment the fastener 600 is supported and attached to the bone by an endoscopic screwdriver apparatus 660, illustrated in FIGS. 28-29. The screwdriver 660 includes a proximal handle portion 662 (illustrated in dashed line), an elongated body portion 664, and a distal tool portion 666.

Figure 29:
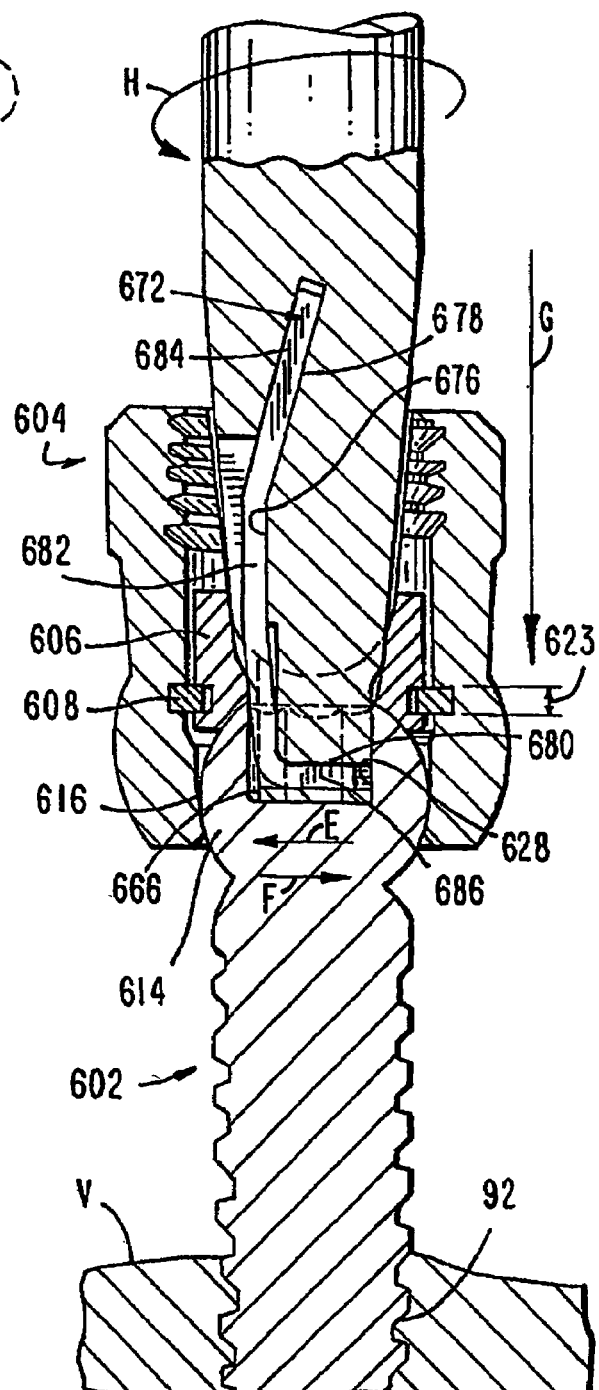
FIG. 29 is an enlarged sectional view of the fastener of FIGS. 26-27 coupled with the surgical instrument of FIG. 28, illustrating one embodiment of a stage of one embodiment of a method for treating the spine of a patient.

The distal tool portion 666, as illustrated in greater detail in FIG. 29 includes a substantially hexagonal outer periphery which is received in the substantially hexagonal recess 628 in the joint portion 614 of the screw member 602. A spring member at the distal tool portion 666 releasably engages the hexagonal recess 628 of the screw member 602 to support the fastener 600 during insertion and tightening. In the illustrated embodiment, a spring member 672 is configured to engage the side wall of the recess 628. More particularly, a channel/ groove is provided in the tip portion 666 for receiving the spring member 672. The channel/groove includes a medial longitudinal notch portion 676, a proximal, angled channel portion 678, and a distal substantially transverse channel portion 680. The spring member 672 is preferably manufactured from stainless steel and has a medial portion 682 that is partially received in the longitudinal notch portion 676, an angled proximal portion 684 which is fixedly received in the angled channel portion 678, and a transverse distal portion 686 which is slidably received in the transverse channel 680. The medial portion 682 of the spring member 672 is partially exposed from the distal tip portion 666 and normally biased in a transverse outward direction with respect to the longitudinal axis (indicated by arrow E), in order to supply bearing force against the wall of the recess 628. Alternatively the distal tip portion of the screw driver may be magnetized in order to hold the screw portion 602. Similarly, the distal tip portion may include a ball bearing or similar member which is normally biased in a radially outward direction to engage the interior wall of the recess 628 to secure the fastener 600 to the screwdriver distal tip 666.

The insertion of the fastener 600 into the prepared hole 92 may be achieved by insertion of screwdriver 660 into conduit 20 (indicated by arrow G). This procedure may be visualized by the use of the endoscope 500 in conjunction with fluoroscopy. The screw portion 602 is threaded into the prepared hole 92 by the endoscopic screwdriver 660 (indicated by arrow H). The endoscopic screwdriver 660 is subsequently separated from the fastener 600, by applying a force in the proximal direction, and thereby releasing the distal tip portion 666 from the hexagonal recess 628 (e.g., causing the transverse distal portion 686 of the spring member 672 to slide within the transverse recess 680 against the bias, indicated by arrow F), and removing the screwdriver 660 from the expandable conduit 20. An alternative method may use a guidewire, which is fixed in the hole 92, and a cannulated screw which has an internal lumen (as is known in the art) and is guided over the guidewire into the hole 92. The screwdriver would be cannulated as well to fit over the guidewire.

For a two-level fixation, it may be necessary to prepare several holes and attach several fasteners 600. Typically, the expandable conduit 20 will be sized in order to provide simultaneous access to all vertebrae in which the surgical procedure is being performed. In some cases, however, additional enlargement or repositioning of the distal portion of the expandable conduit may be required in order to have sufficient access to the outer vertebrae, e.g., the L4 and S1 vertebrae. In the illustrated embodiment, the expander apparatus 200 may be repeatedly inserted into the expandable conduit 20 and expanded in order to further open or position the skirt portion 24. In one procedure, additional fasteners are inserted in the L4 and S1 vertebrae in a similar fashion as the fastener 600 inserted in to the L5 vertebra as described above. (When discussed individually or collectively, a fastener and/or its individual components will be referred to by the reference number, e.g., fastener 600, housing 604, and all fasteners 600. However, when several fasteners and/or their components are discussed in relation to one another, an alphabetic subscript will be used, e.g., fastener 600*a* is moved towards fastener 600*b*.)

In a further stage of the procedure, the housing portions 604 of the fasteners 600 are substantially aligned such that their upright portions 630 and 631 face upward, and the notches 632 are substantially aligned to receive the elongated member 650 therein. The frictional mounting of the housing 604 to the screw member 602, described above, allows the housing 604 to be temporarily positioned until a subsequent tightening step, described below. Positioning of the housing portions 604 may be performed by the use of an elongated surgical instrument capable of contacting and moving the housing portion to the desired orientation. One such instrument for positioning the housings 604 is a grasper apparatus 700, illustrated in FIG. 30. The grasper apparatus 700 includes a proximal handle portion 702, an elongated body portion 704, and distal nose portion 706. The distal nose portion 706 includes a pair of grasping jaws 708a and 708b, which are pivotable about pin 710 by actuation of the proximal handle portion 702. The grasping jaws 708a and 708b are illustrated in the closed position in FIG. 30. As is known in the art, pivoting the movable handle 714 towards stationary handle 714 causes longitudinal movement of actuator 716, which in turn pivots the jaw 708b towards an open position (illustrated in dashed line). The biasing members 718 and 720 are provided to return the handles 712 and 714 to the open position and bias the jaws 708a and 708b to the closed position.

A subsequent stage in the process is the insertion of the elongated member 650 into the expandable conduit. The elongated member 650 is manufactured from a biocompatible material and must be sufficiently strong to maintain the positioning of the vertebrae, or other body structures. In the exemplary embodiment, the elongated members 650 are manufactured from Titanium 6/4 or titanium alloy. Alternatively, the elongated member 650 may be manufactured from stainless steel or other suitable material. The radii and length of the elongated members 650 are selected by the physician to provide the best fit for the positioning of the screw heads. Such selection may be performed by placing the elongated member 650 on the skin of the patient overlying the location of the fasteners and viewed fluoroscopically. For example, a 70 mm preformed rod having a 3.5" bend radius may be selected for the spinal fixation.

Figure 30:
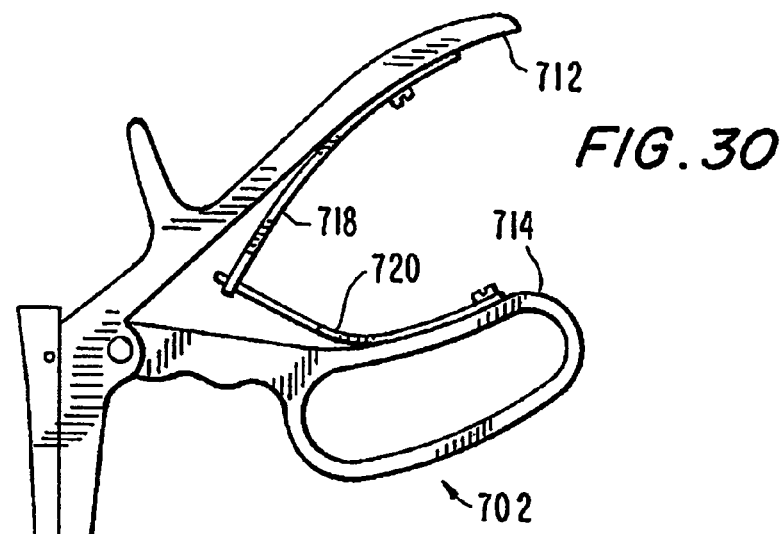
FIG. 30 is side view of one embodiment of another surgical instrument.

The elongated member 650 is subsequently fixed to each of the fasteners 600, and more particularly, to the housings 604 of each fastener 600. The grasper apparatus 700, described above, is also particularly useful for inserting the elongated member 650 into the expandable conduit 20 and positioning it with respect to each housing 604. As illustrated in FIG. 30, the jaws 708a and 708b of the grasper apparatus 700 each has a curved contact portion 722a and 722b for contacting and holding the outer surface of the elongated member 650.

Figure 31:
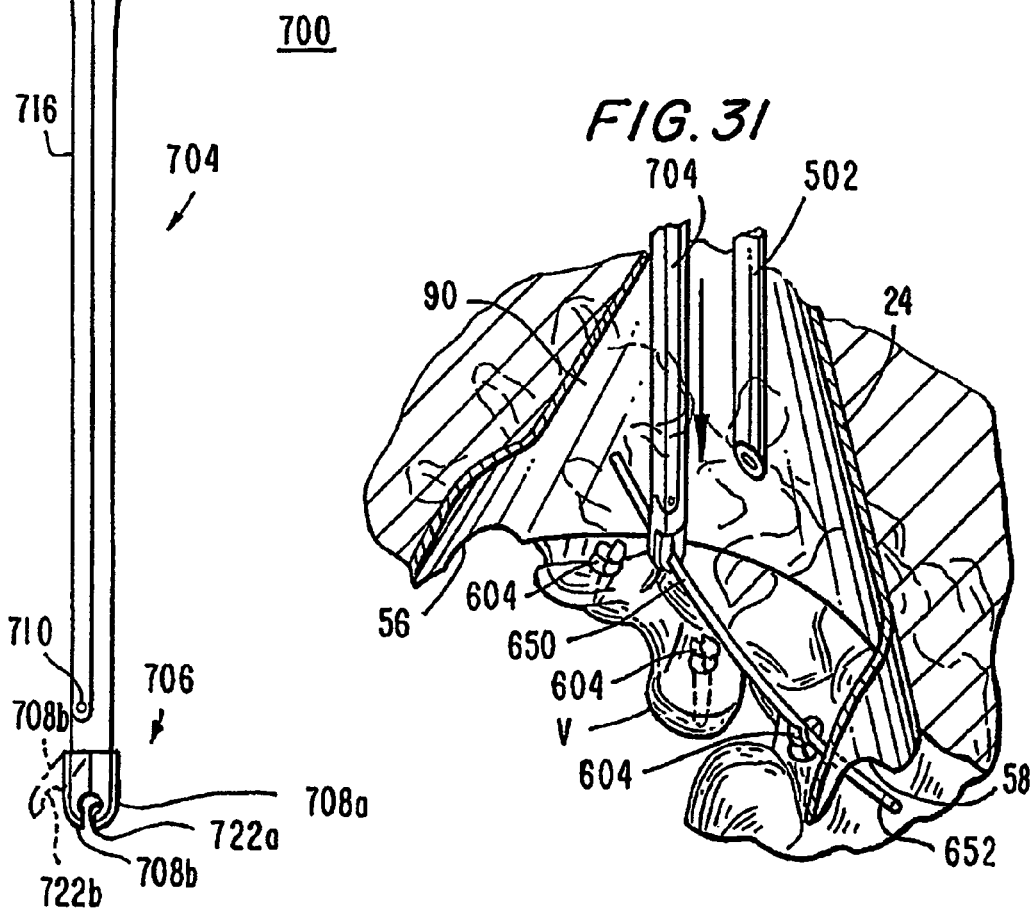
FIG. 31 is a partial sectional view of one embodiment of a stage of one embodiment of a method for treating the spine of a patient.

As illustrated in FIG. 31, the grasper apparatus 700 may be used to insert the elongated member 650 into the operative space 90 defined at least partially by the skirt portion 24 of the expandable conduit 20. The cut-out portions 56 and 58 provided in the skirt portion 24 assist in the process of installing the elongated member 650 with respect to the housings 604. The cut-out portions 56 and 58 allow an end portion 652 of the elongated member 650 to extend beyond the operative space without raising or repositioning the skirt portion 24. The elongated member 650 is positioned within the recesses in each housing 604 defined by grooves 632 disposed between upright members 630 and 631. The elongated member 650 is positioned in an orientation substantially transverse to the longitudinal axis of each housing 604.

Further positioning of the elongated member 650 may be performed by guide apparatus 800, illustrated in FIG. 32. Guide apparatus 800 is useful in cooperation with an endoscopic screwdriver, such as endoscopic screwdriver 660 (illustrated in FIG. 28), in order to position the elongated member 650, and to introduce and tighten the cap screw 610, described above and illustrated in FIG. 27. Tightening of the cap screw 610 with respect to the housing 604 fixes the orientation of the housing 604 with respect to the screw portion 602 and fixes the position of the elongated member 650 with respect to the housing 604.

In the illustrated embodiment, the guide apparatus 800 has a proximal handle portion 802, an elongated body portion 804, and a distal tool portion 806. The elongated body portion 804 defines a central bore 808 (illustrated in dashed line) along its longitudinal axis 810. The central bore 808 is sized and configured to receive the endoscopic screwdriver 660 and cap screw 610 therethrough. In the exemplary embodiment, the diameter of the central bore 808 of the elongated body portion 804 is about 0.384-0.388 inches in diameter, and the external diameter of the endoscopic screwdriver 660 (FIG. 28) is about 0.25 inches. The proximal handle portion 802 extends transverse to the longitudinal axis 810, which allows the physician to adjust the guide apparatus 800 without interfering with the operation of the screwdriver 660.

The distal portion 806 of the apparatus includes several semicircular cut out portions 814 which assist in positioning the elongated member 650. As illustrated in FIG. 33, the cut out portions 814 are sized and configured to engage the surface of elongated member 650 and move the elongated member 650 from an initial location (illustrated in dashed line) to a desired location.

As illustrated in FIG. 34, the guide apparatus 800 is used in cooperation with the endoscopic screwdriver 660 to attach the cap screw 610. The distal end of the body portion 804 includes a pair of elongated openings 816, which permit the physician to endoscopically view the cap screw 610 retained at the distal tip 666 of the endoscopic screw driver 660.

The guide apparatus 800 and the endoscopic screwdriver 660 may cooperate as follows. The guide apparatus 800 is configured to be positioned in a surrounding configuration with the screwdriver 600. In the illustrated embodiment, the body portion 804 is configured for coaxial placement about the screwdriver 660 in order to distribute the contact force of the guide apparatus 800 on the elongated member 650. The distal portion 806 of the guide apparatus 800 may bear down on the elongated member 650 to seat the elongated member 650 in the notches 632 in the housing 604. The "distributed" force of the guide apparatus 800 may contact the elongated member 650 on at least one or more locations. In addition, the diameter of central bore 808 is selected to be marginally larger than the exterior diameter of cap screw 610, such that the cap screw 610 may freely slide down the central bore 808, while maintaining the orientation shown in FIG. 34. This configuration allows the physician to have effective control of the placement of the cap screw 610 into the housing 604. The cap screw 610 is releasably attached to the endoscopic screwdriver 660 by means of spring member 672 engaged to the interior wall of hexagonal recess 611 as it is inserted within the bore 808 of the body portion 804 of guide apparatus 800. The cap screw 610 is attached to the housing 604 by engaging the threads 615 of the cap screw 610 with the threads 634 of the housing.

Figure 35:
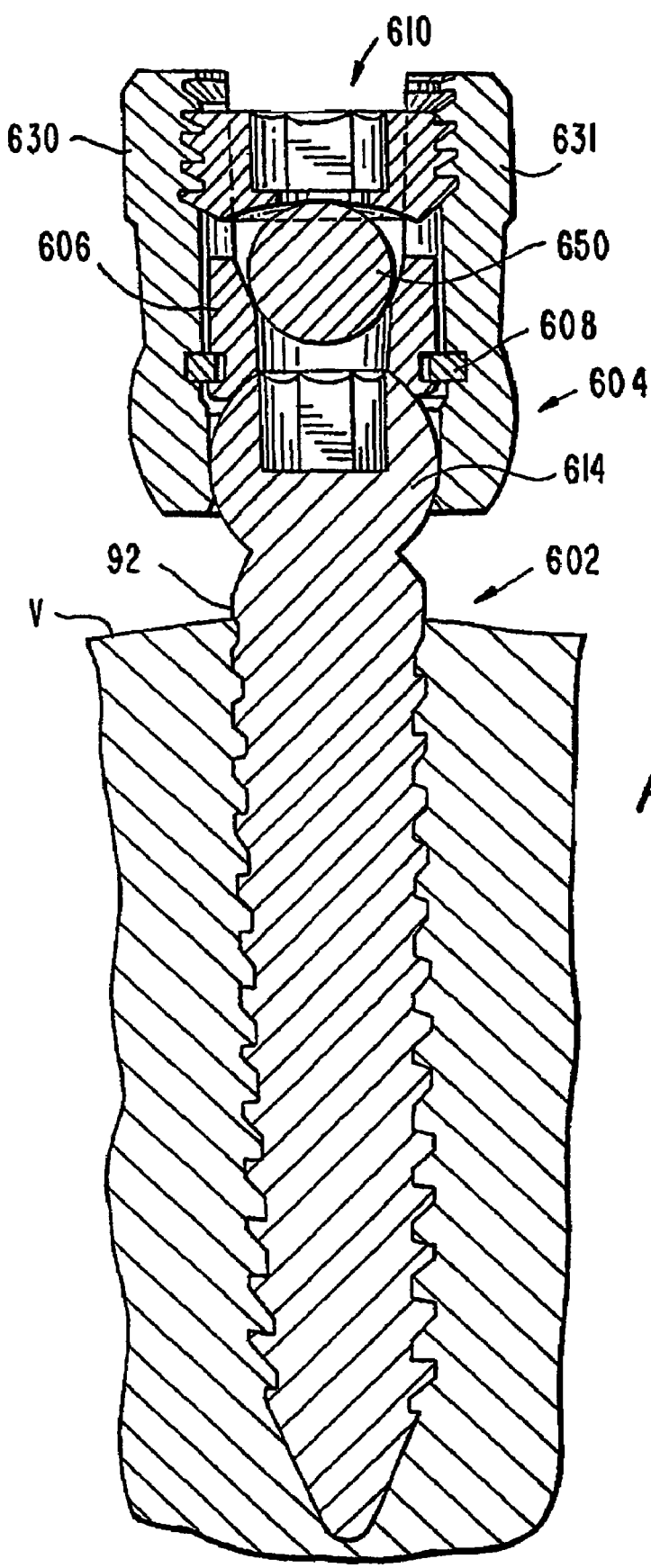
FIG. 35 is an enlarged sectional similar to FIG. 34, illustrating one embodiment of a stage of one embodiment of a method for treating the spine of a patient.

As illustrated in FIG. 35, tightening of the cap screw 610 fixes the assembly of the housing 604 with respect to the elongated member 650. In particular, the distal surface of the cap screw 610 provides a distal force against the elongated member 650, which in turn drives the spacer member 606 against the joint portion 614 of the screw portion 602, which is consequently fixed with respect to the housing 604.

If locations of the vertebrae are considered acceptable by the physician, then the fixation procedure is substantially complete once the cap screws 610 have been attached to the respective housings 604, and tightened to provide a fixed structure as between the elongated member 650 and the various fasteners 600. However, if compression or distraction of the vertebrae with respect to one another is required additional apparatus would be used to shift the vertebrae prior to final tightening all of the cap screws 610.

Figures 36, 37:
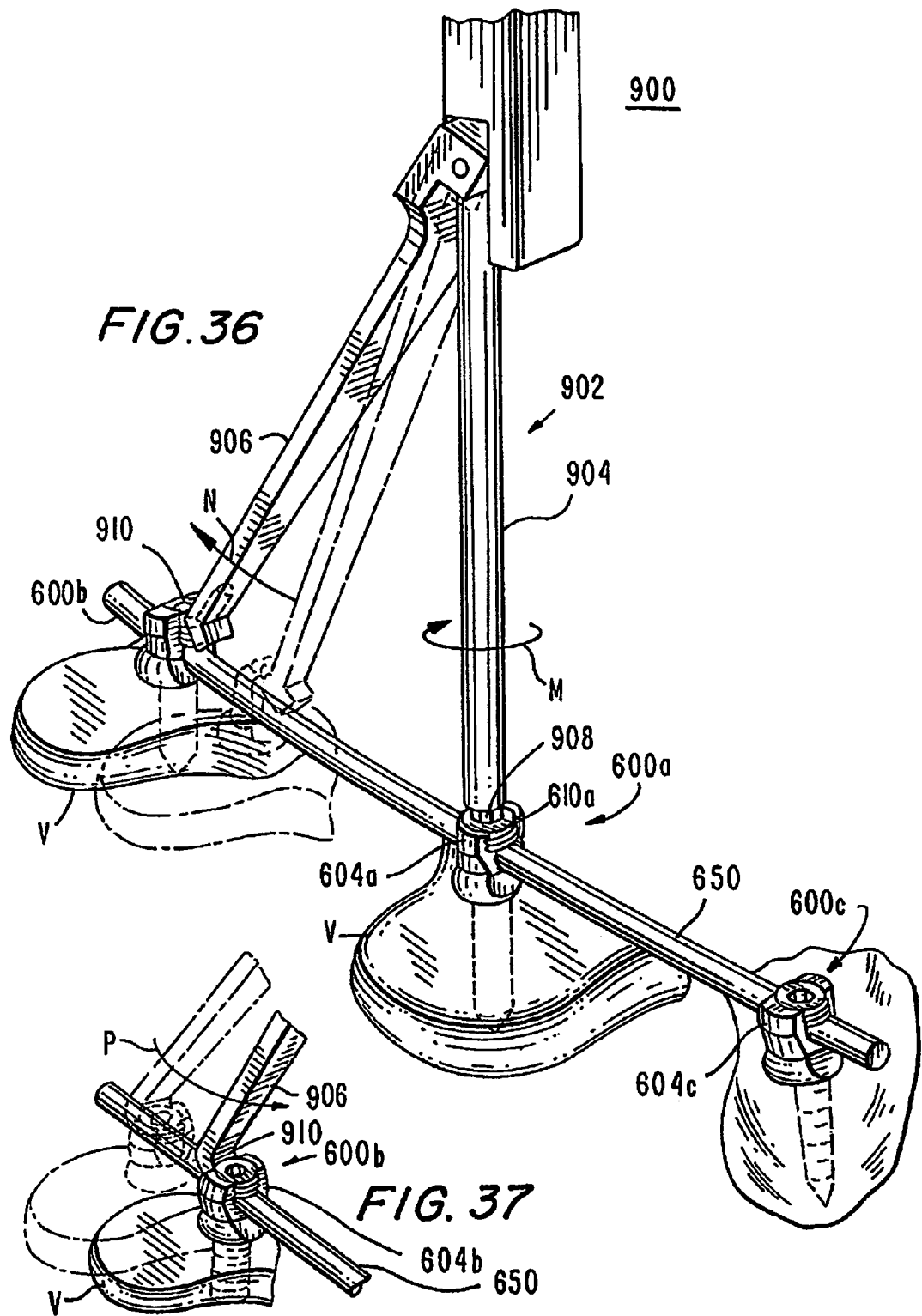
FIG. 36 is an enlarged view in partial section illustrating one embodiment of a stage of one embodiment of a method for treating the spine of a patient.
FIG. 37 is a partial view of illustrating one embodiment of a stage of one embodiment of a method for treating the spine of a patient.

In the illustrated embodiment, this step is performed with a surgical instrument, such as compressor-distractor instrument 900, illustrated in FIG. 36, which is useful to relatively position bone structures in the cephcaudal direction and to fix their position with respect to one another. Thus, the compressor-distractor instrument 900 has the capability to engage two fasteners 600 and to space them apart while simultaneously tightening one of the fasteners to fix the spacing between the two vertebrae, or other bone structures. Moreover, the compressor-distractor instrument 900 may also be used to move two fasteners 600, and the vertebrae attached thereto into closer approximation and fix the spacing therebetween.

The distal tool portion 902 of the compressor-distractor instrument 900 is illustrated in FIG. 36. (Further details of the compressor-distractor apparatus is described in co-pending U.S. application Ser. No. 10/178,875, filed Jun. 24, 2002, entitled "Surgical Instrument for Moving Vertebrae," which is incorporated by reference in its entirety herein.) The distal tool portion 902 includes a driver portion 904 and a spacing member 906. The driver portion 904 has a distal end portion 908 with a plurality of wrenching flats configured to engage the recess 611 in the proximal face of the cap screw 610, and to apply torque to the cap screw. The driver portion 904 is rotatable about the longitudinal axis (indicated by arrow M) to rotate the cap screw 610 relative to the fastener 600. Accordingly, the driver portion 904 can be rotated to loosen the cap screw 610 on the fastener 600 and permit movement of the elongated member 650 connected with the vertebra relative to the fastener 600 connected with the vertebra. The cap screw 610 can also be rotated in order to tighten the cap screw 610 and clamp the elongated member 650 to the fastener 600.

The distal tool portion 902 may also include a spacing member, such as spacing member 906, which engages an adjacent fastener 600b while driver member 904 is engaged with the housing 604a to move the fastener 600b with respect to the fastener 600a. In the exemplary embodiment, spacing member 906 is a jaw portion which is pivotably mounted to move between a first position adjacent the driver portion and a second position spaced from the driver portion, as shown in FIG. 36. The distal tip 910 of the spacing member 906 is movable relative to the driver portion 904 in a direction extending transverse to the longitudinal axis.

As illustrated in FIG. 36, the spacer member 906 can be opened with respect to the driver portion 904 to space the vertebrae further apart (as indicated by arrow N). The distal portion 910 of the spacer member 906 engages the housing 604b of fastener 600b and moves fastener 600b further apart from fastener 600a to distract the vertebrae. Where the vertebrae are to be moved closer together, e.g. compressed, the spacer member 906 is closed with respect to the driver portion 904 (arrow P), as illustrated in FIG. 37. The distal portion 610 of spacer member 606 engages housing 604b of fastener 600b and moves fastener 600b towards fastener 600a. When the spacing of the vertebrae is acceptable to the physician, the cap screw 610a is tightened by the driver member 904, thereby fixing the relationship of the housing 604a with respect to elongated member 650, and thereby fixing the position of the vertebrae, or other bone structures, with respect to one another.

Once the elongated member 650 is fixed with respect to the fasteners 600, the procedure is substantially complete. The surgical instrumentation, such as the endoscope 500 is withdrawn from the surgical site. The expandable conduit 20 is also withdrawn from the site. The muscle and fascia typically close as the expandable conduit 20 is withdrawn through the dilated tissues in the reduced profile configuration. The fascia and skin incisions are closed in the typical manner, with sutures, etc. The procedure described above may be repeated for the other lateral side of the same vertebrae, if indicated.

II. Other Fixation Procedures Performed with the Systems Described Herein

As discussed above, the systems disclosed herein provide access to a surgical location at or near the spine of a patient to enable procedures to be performed on the spine. These procedures can be applied to one or more vertebral levels. Additional procedures and combinations of procedures that may be performed using the systems described herein are discussed below. These procedures include translaminar facet screw fixation and transfacet pedicle screw fixation to stabilize two adjacent vertebrae. Both of the above mentioned procedures are generally transfacet fixation procedures. Translaminar includes penetration by the fastener through portions of both the spinous process, the lamina, and the facet joint. They can be used alone or in conjunction with the fixation techniques including but not limited to bone graft materials or fixation devices placed in the actual disc space to promote fusion of the vertebrae.

In one embodiment stabilizing two adjacent vertebrae, an access device is inserted into the patient to provide access to a spinal location, as described above. A variety of anatomical approaches may be used to provide access to a spinal location using the expandable conduit. The access device preferably is inserted generally posteriorly. As used herein the phrase "generally posteriorly" is used in its ordinary sense and is a broad term that refers to a variety of surgical approaches to the spine that may be provided from the posterior side, i.e., the back, of the patient, and includes, but is not limited to, posterior, postero-lateral, and transforaminal approaches. Any of the access devices described or incorporated herein, such as the expandable conduit, could be used. Referring to the proximal and distal ends of these access devices, they may be circular, oblong, oval or another shape. The shape of one end need not determine the shape of the other. The term "oblong" is used in its ordinary sense (i.e. having an elongated form) and is a broad term and it includes a structure having a dimension, especially one of two perpendicular dimensions, such as, for example, width or length, that is greater than another. The term "oval" is used in its ordinary sense (i.e., egg like or elliptical) and is a broad term and includes oblong shapes having curved protions and oblong shapes having parallel sides and curved portions.

Further details of various additional embodiments of the access device may be found in U.S. patent application Ser. No. 10/678,744, filed Oct. 2, 2003, entitled MINIMALLY INVASIVE ACCESS DEVICE AND METHOD, and in U.S. Provisional Patent Application No. _____, filed Oct. 22, 2003, both of which are hereby incorporated by reference herein in their entirety.

The distal end of the access device may be placed at the desired surgical location, e.g., adjacent the spine of the patient, with a central region of the access device over a first vertebrae. In one procedure, the distal end of the access device is inserted until it contacts at least a portion of at least one of the vertebrae being treated or at least a portion of the spine. In another procedure, the distal end of the access device is inserted until it contacts a portion of the spine and then is withdrawn a small amount to provide a selected gap between the spine and the access device. In other procedures, the access device may be inserted a selected amount, but not far enough to contact the vertebrae being treated, the portion of the vertebrae being treated, or the spine.

The access device may be configured, as described above, to provide increased access to the surgical location. The access device can have a first configuration for insertion to the surgical location over the first vertebra and a second configuration wherein increased access is provided to the target vertebrae. The first configuration may provide a first cross-sectional area at a distal portion thereof. The second configuration may provide a second cross-sectional area at the distal portion thereof. The second cross-sectional area preferably is enlarged compared to the first cross-sectional area. In some embodiments, the access device may be expanded from the first configuration to the second configuration to provide access to the adjacent vertebrae either above the first vertebra, below the first vertebra, or both.

A. Transfacet Spinal Stabilization using Translaminar Fact Screw Fixation

In one embodiment of this invention, translaminar facet screw fixation is achieved using one or more access devices to achieve access to the spine. Translaminar facet screw fixation includes a stabilization fastener through portions of the spinous process, the lamina and the facet joint. There are multiple ways of achieving access using the access devices. In one embodiment, access is gained using two devices, one access device on the ipsalateral side and one on the contralateral side of the spine. It is useful to define several axes in FIG. 38 to describe the placement of the access device relative to the spine. A spinal axis S runs generally along the spine of the patient from head to toe, or top to bottom of the figure. A transverse axis T runs generally laterally across the spine from right to left in the figure. A posterior axis P runs generally in line with the spinous process out from the page. In this embodiment, each access device preferably enters from a generally posterior approach and rests at or near the desired spinous process, preferably at a first angle A1 of approximately 0 to 90 from the plane defined by the spinal axis S and the posterior axis P (hereinafter "S-P plane"), a second angle A2 of approximately 0 to 60 from the plane defined by the transverse axis T and the posterior axis P (hereinafter "T-P plane"), and a third angle A3 (not shown) of approximately 0 to 90 from the plane defined by the spinal axis S and the transverse axis T (hereinafter "S-T plane"). More preferably, the first angle A1 is approximately 25 to 65 from S-P plane, the second angle A2 is 15 to 45 from the T-P plane, and the third angle A3 is 25 to 65 from the S-T plane. These angles are largely determined by the structure of the individual spine that the doctor addresses in each operation and should not be considered strict requirements for this embodiment.

Figure 38:
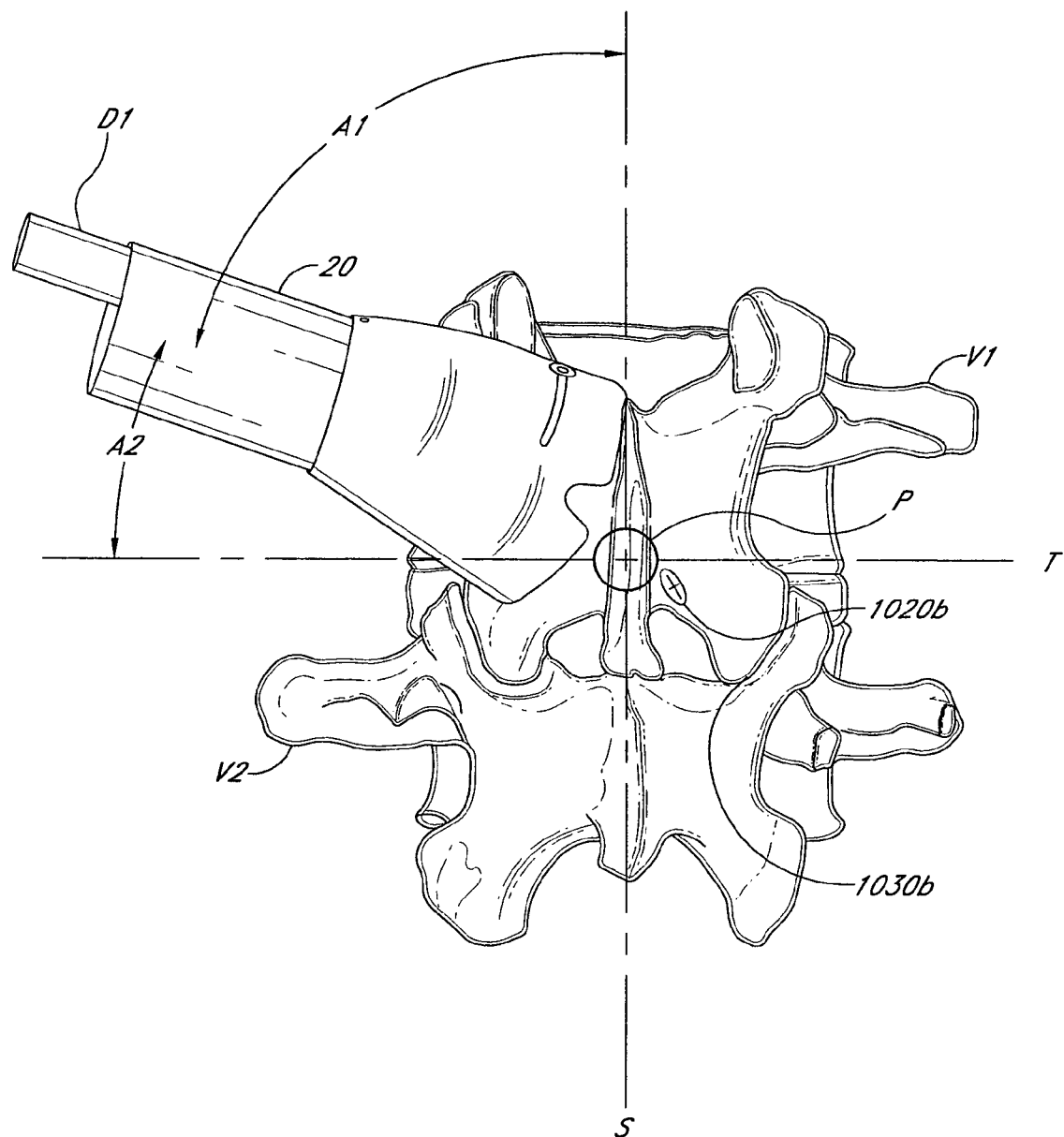
FIG. 38 is a view illustrating the placement of an access device in one embodiment of a fixation method.

FIG. 38 shows one placement of the access device 20 to allow insertion of the fasteners and other tools used for the procedure. In this embodiment, an access device 20 is envisioned with a diameter of 16-24 mm with an actuatable section expandable to between 25 and 40 mm. This and other embodiments may use an access device 20 of greater or smaller diameter. Once the access device 20 is inserted, its distal end may be actuated from a first configuration to a second configuration to allow sufficient space for the physician to manipulate the tools and equipment to effect a proper stabilization. A similar procedure is used to gain access to the spine through the access device 20 on the other side of the spine. In all cases, the access device 20 may be used either with or without an endoscope, allowing visualization of the surgical location through direct view or an enhanced means depending upon the physician's preference.

In another embodiment, the access device 20 can be expanded to provide access to more than one spinous process 1010, opening the door to multilevel fixations. The approach would be similar to the above-described approach; however, the actuated portion of the access device would be expanded to reveal multiple vertebrae.

Figure 39:
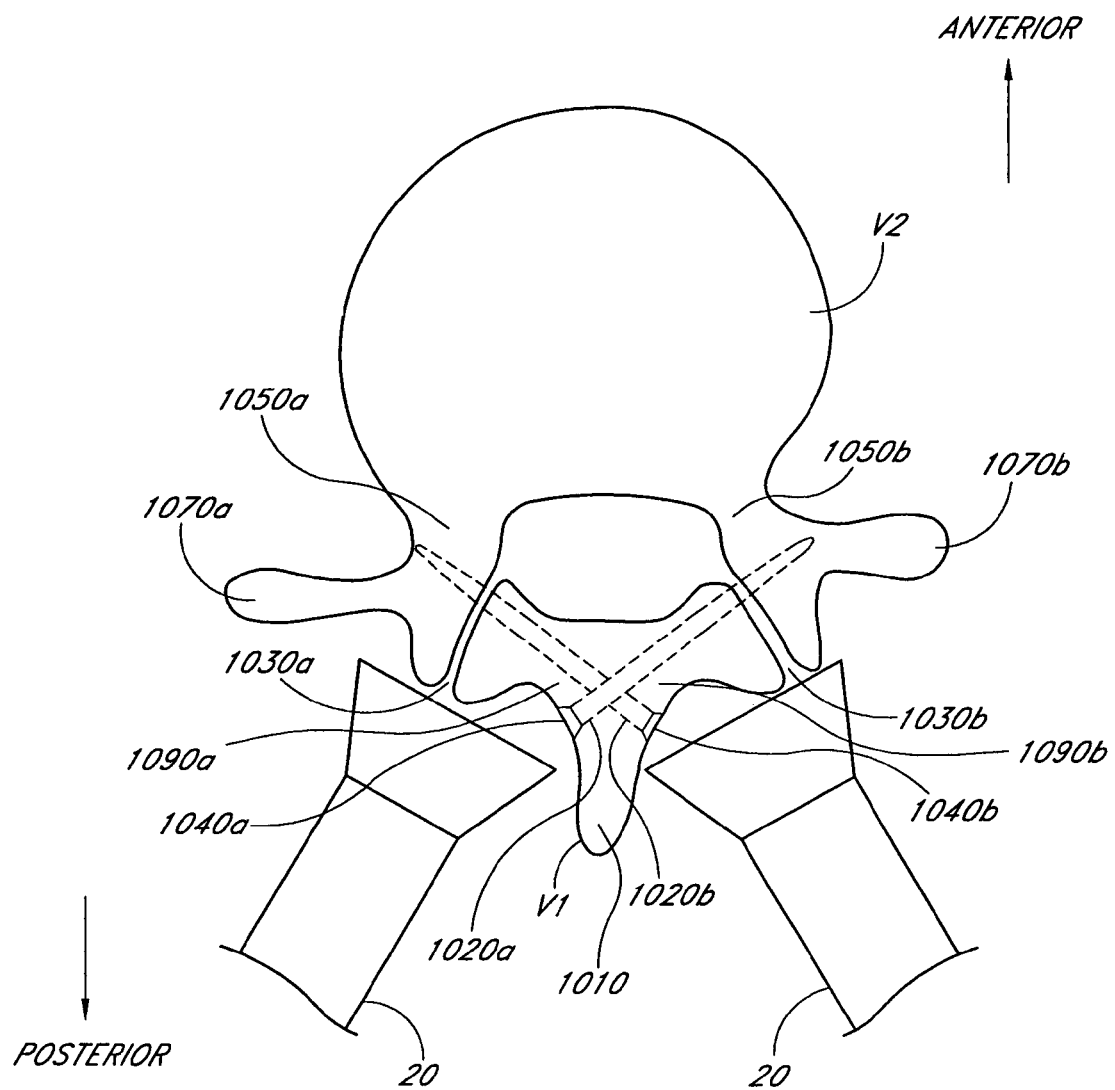
FIG. 39 is a view illustrating one embodiment of a fixation method.
Figure 40:
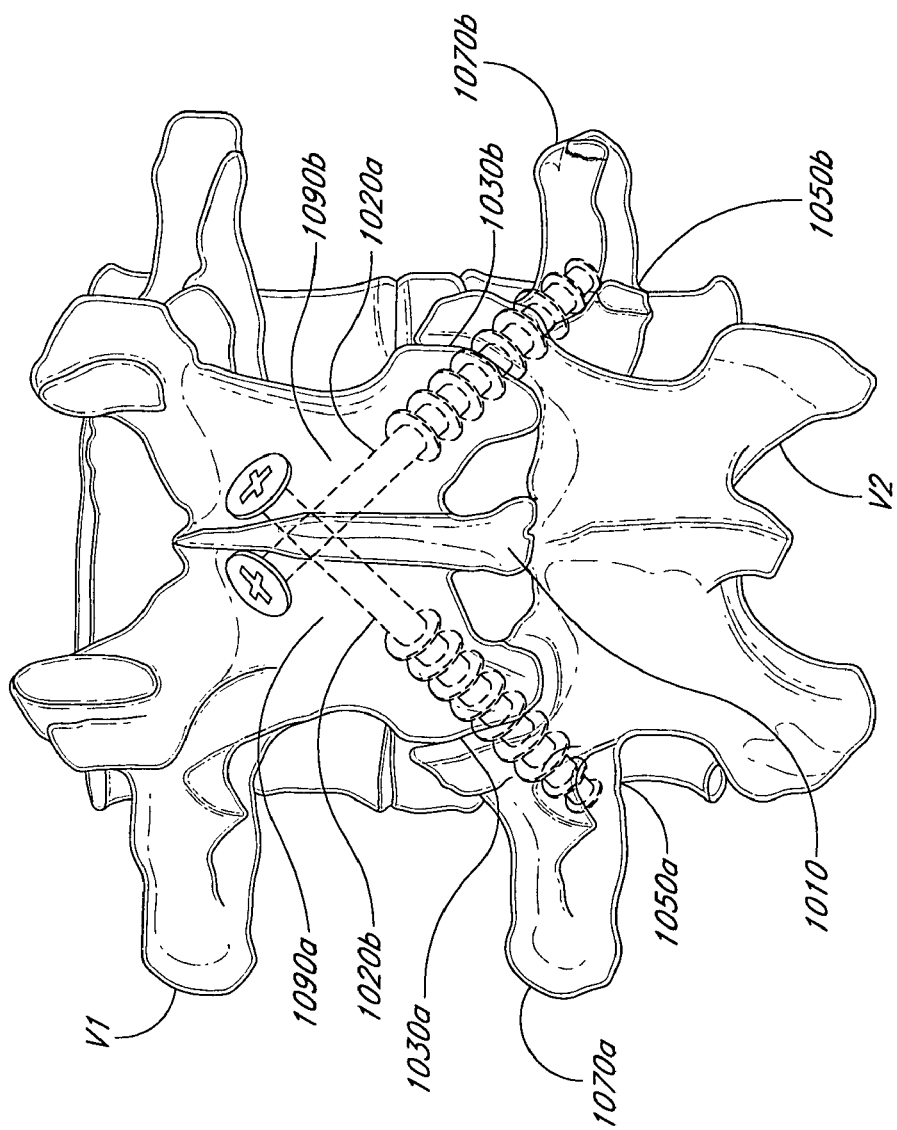
FIG. 40 is a view illustrating one embodiment of a fixation method.

With the access device 20 oriented as described above, the doctor can then stabilize the vertebrae using translaminar facet screw fixation. FIGS. 39 and 40 illustrate how the vertebrae are stabilized using translaminar facet screw fixation. Two fasteners 1020a and 1020b are used to secure the vertebrae. In a preferred embodiment, the physician will initiate the procedure by accessing the spine through the access device 20 and scoring the bone at or near the base of the spinous process 1010 with a drill, wire, probe, or some other similar device known in the art, to offer a starting point to create a translaminar tunnel 1060. The bone through which the fasteners are to run may be optionally tapped, pre-drilled or marked in some other manner to allow for ease and accuracy when inserting the fasteners 1020a and 1020b.

Figure 41:
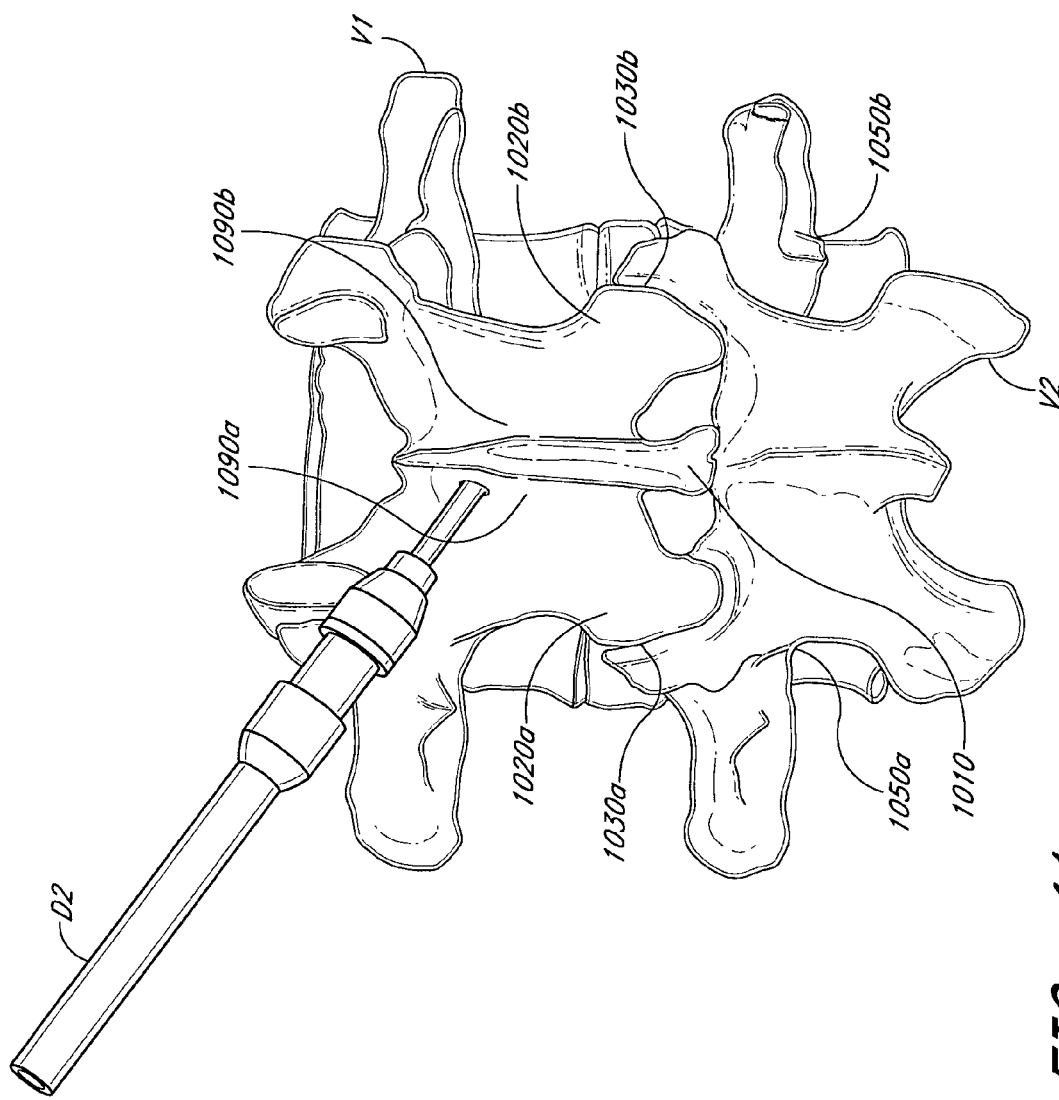
FIG. 41 is a view of the spine illustrating a method for creating a translaminar tunnel.
Figure 42:
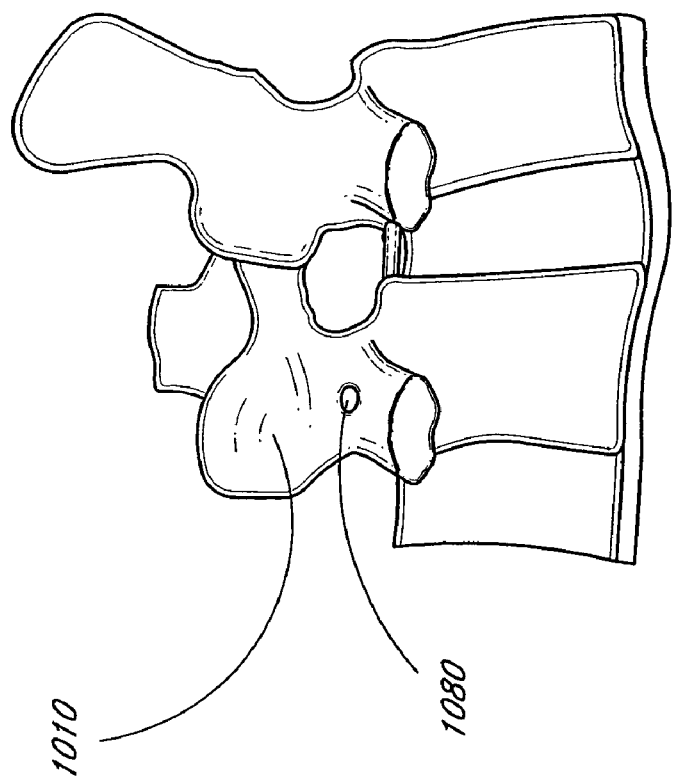
FIG. 42 is a view of the spine illustrating a translaminar tunnel opening.

In a preferred embodiment, a translaminar tunnel 1060 is created with a drill D1 as depicted in FIG. 41, the diameter of said tunnel 1060 being small enough to allow sufficient purchase for the fasteners to actively engage the bone material while being large enough to allow for an accurate insertion of the fastener. The tunnel 1060 travels through a portion of the spinous process 1010 and into a portion of the facet joint 1030a. It may also pass through a portion of the lamina 1090a at the base of the spinous process 1010. Further, the drill D1 may be advanced through an access device (not shown) as described above. The translaminar tunnel 1060 may be created using a wire, probe, drill, or other similar device known in the art. In a preferred embodiment, the fastener 1020a used in this procedure provide the stabilization required to allow the bone of the adjacent vertebrae to fuse. The actuated access device 20 provides additional space to the operating physician while minimizing trauma to the surrounding tissue. FIG. 42 shows the entry hole 1080 of a translaminar tunnel after the drill D1 has been removed.

With the translaminar tunnel 1060 in place, the physician can, though an access device, introduce a first fastener 1020a to the desired vertebrae. This fastener 1020a is secured through the spinous process 1010 of the first vertebrae V1, through the facet joint 1030b on the contralateral side from the insertion point 1040a and into the base 1050b of the pedicle of the second vertebrae V2 using a screw driver or similar mechanical device D2 for assisted insertion passing through the access device 20 and coming into mechanical contact with the fastener 1020a. In other embodiments, the fastener 1020a may reach the apex of the pedicle or may not enter the pedicle at all, rather travelling though the lateral facet near the transverse process 1070b.

Figure 43:
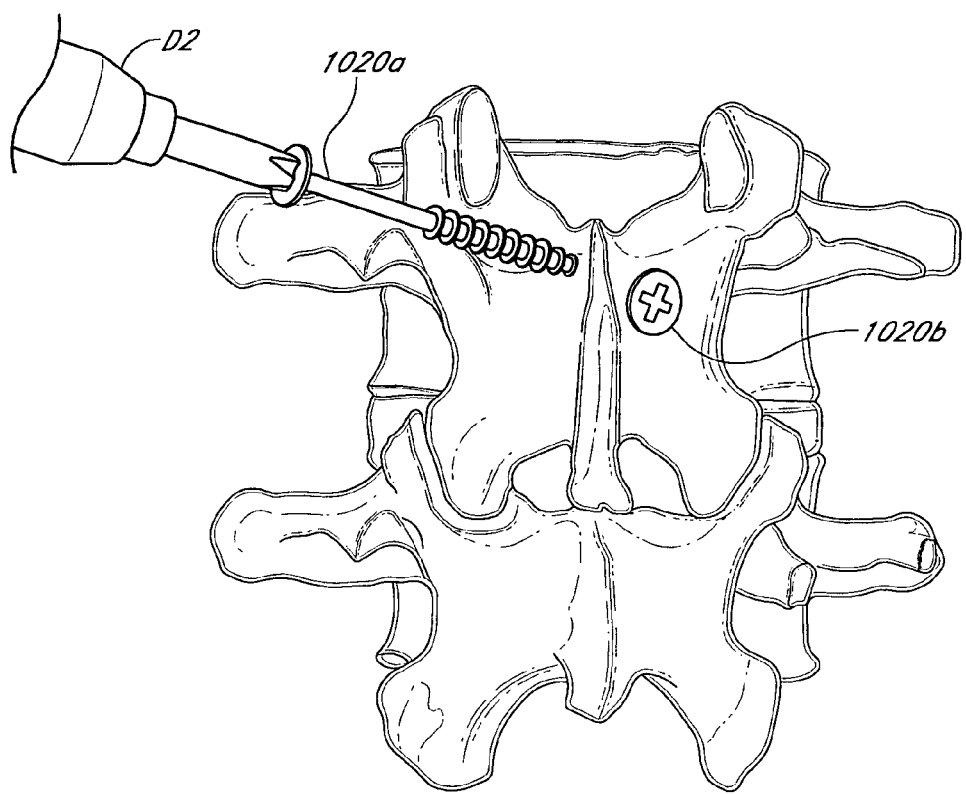
FIG. 43 is a view of the spine showing a fastener being inserted in a transfacet fixation technique.
Figure 44:
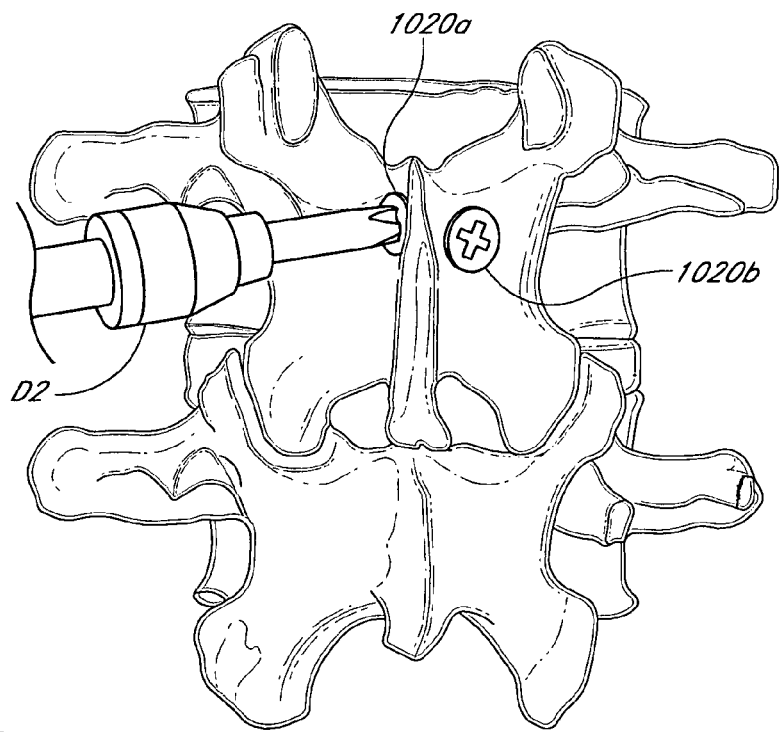
FIG. 44 is a view of two fasteners fully secured through the spine in one embodiment of a transfacet fixation method.

Access is gained though a second access device 20 as described above and a second fastener 1020b is similarly inserted through the access device 20 and secured to the vertebrae through the spinous process 1010 and a portion of the lamina 1090a of the first vertebrae V1, this time at insertion point 1040b, traveling through the facet joint 1030a on the side opposite the insertion point 1040b and into the base 1050a of the pedicle of the second vertebrae V2. In alternative embodiments, the fastener 1020b used to secure the vertebrae may reach other portions of the pedicle other than the base, and/or may not reach the pedicle at all. Alternative embodiments may have the fastener travel through the lateral facet near the transverse process or any combination of this with the above-discussed portions of the vertebrae. These fasteners 1020a and 1020b may comprise screws, straight pins or tapered pins pressed into or bonded to the bone such that they travel through the two vertebrae securing them together. In addition, said fasteners 1020a and 1020b may be composed of a number of biocompatible, stiff materials, including metal material, polymeric material, ceramic material, or other synthetic or naturally stiff material with similar characteristics. In a preferred embodiment, the fasteners 1020a and 1020b are screws made of a metallic material. FIG. 43 shows a fastener 1020a being inserted into the vertebra V1. FIG. 44 shows both fasteners 1020a and 1020b fully inserted, securing the vertebrae V1 and V2. Translaminar facet screw fixation is further described in an article by F. Magerl entitled "Stabilization of the lower thoracic and lumbar spine with external skeletal fixation." *Clin Orthop* 1984; 189; 125-41, the entirety of which is hereby incorporated by reference.

B. Spinal Stabilization using Transfact Pedicle Screw Fixation

Figure 45:
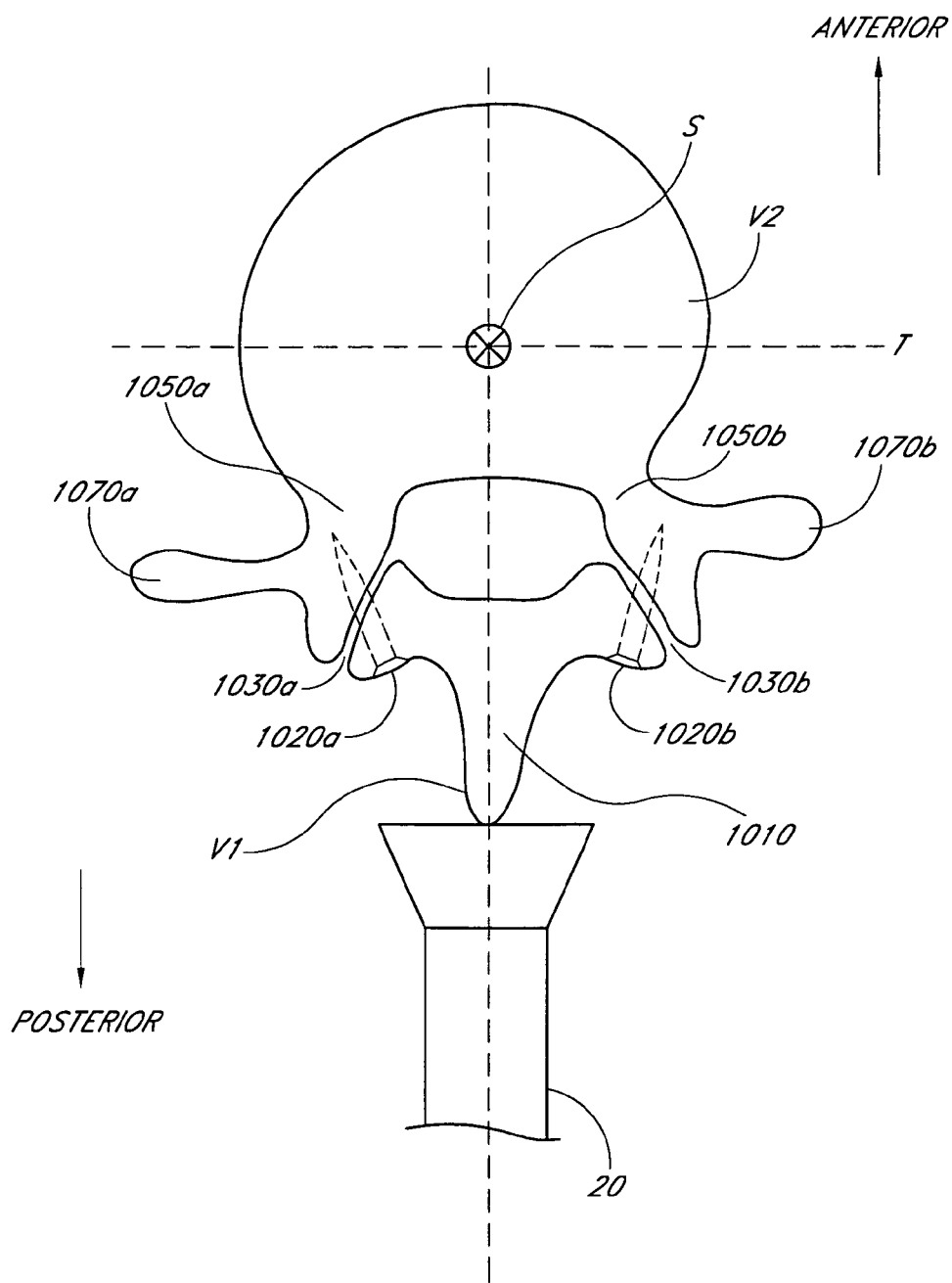
FIG. 45 is view illustrating a possible placement of an access device for one embodiment of a fixation method.

In one embodiment of this invention, transfacet pedicle screw fixation is achieved using one or more access devices to achieve access to the spine. Transfacet pedicle screw fixation includes the penetration of a fastener through at least a portion of the facet joint. There are multiple ways of achieving access using the access devices. In one embodiment, access is gained using one access device to insert all tools and fasteners needed in the procedure. In this embodiment, an access device is envisioned with a diameter of 16-24 mm with an actuatable section expandable to between 25 and 40 mm. This and other embodiments may use an access device of greater or smaller diameter. In this embodiment, the access device preferably enters from a generally posterior approach and rests at or near the desired vertebra. Once the access device is inserted, its distal end may be actuated from a first configuration to a second configuration to allow sufficient space for the physician to manipulate the tools and equipment to effect a proper stabilization. FIG. 45 shows the access device 20 in one possible position at the spine with the distal end actuated to allow more freedom in the surgical space. It would rest at or near the spine at a generally posterior angle to accommodate the angle of insertion necessary to place the fasteners. The spinous process 1010 may be within the working space defined by the access device 20 or adjacent the space. Using the planes of the spine as defined above, the access device 20 in this embodiment would preferably lie at a first angle A1 of approximately 0 to 45 from the S-P plane, a second angle A2 of approximately 0 to 60 from the T-P plane, and a third angle A3 of approximately 45 to 100 from the S-T plane. More preferably, the first angle A1 is approximately 0 to 10 from S-P plane, the second angle A2 is 10 to 45 from the T-P plane, and the third angle A3 is 45 to 80 from the S-T plane. These angles are largely determined by the structure of the individual spine that the doctor addresses in each operation and should not be considered strict requirements for this embodiment. In another embodiment, the access device herein discussed may be expanded to cover multiple vertebrae, allowing application of the transfacet pedicle screw fixation to multiple levels from a single access device. Thus, it is possible to perform this fixation technique using one or more access devices. In all cases, the access device may be used either with or without an endoscope.

Another possible embodiment would place a single access device over multiple vertebrae. The access angle would be similar to the above-described, with the actuated portion of the access device open sufficiently to span two or more spinous processes, thus allowing the physician to fix three vertebra with 2 or more fasteners.

In another embodiment, a separate access device is used on either side of the spinous process to effect the transfacet pedicle screw fixation. In such an embodiment, the access device can be actuated to cover one or more vertebrae per side, allowing for single or multilevel fixation. The approach angle would be similar to that described above with the access device shifted laterally to address specific sides of the vertebrae.

Figure 46:
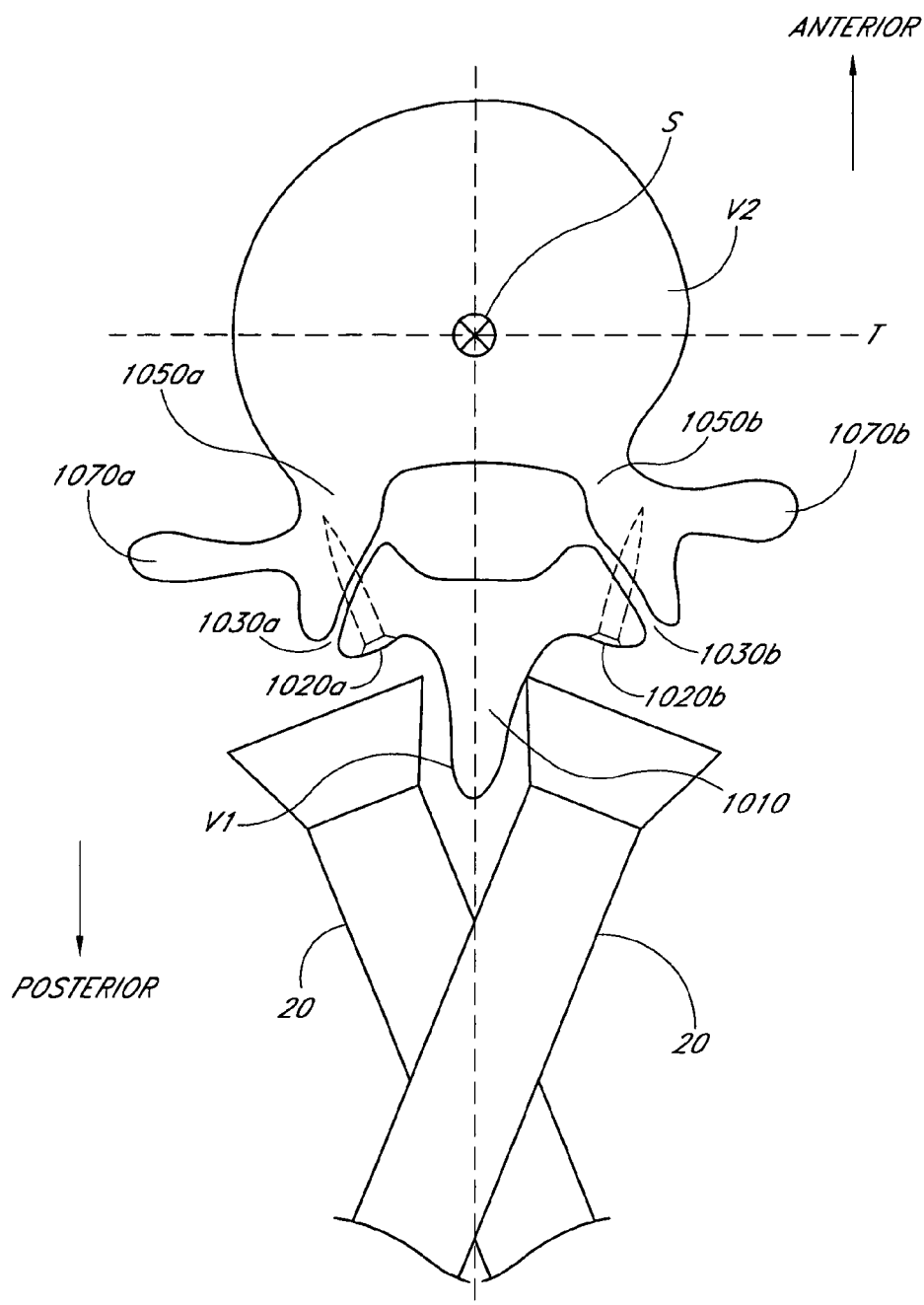
FIG. 46 is a view illustrating one embodiment of a fixation method.
Figure 47:
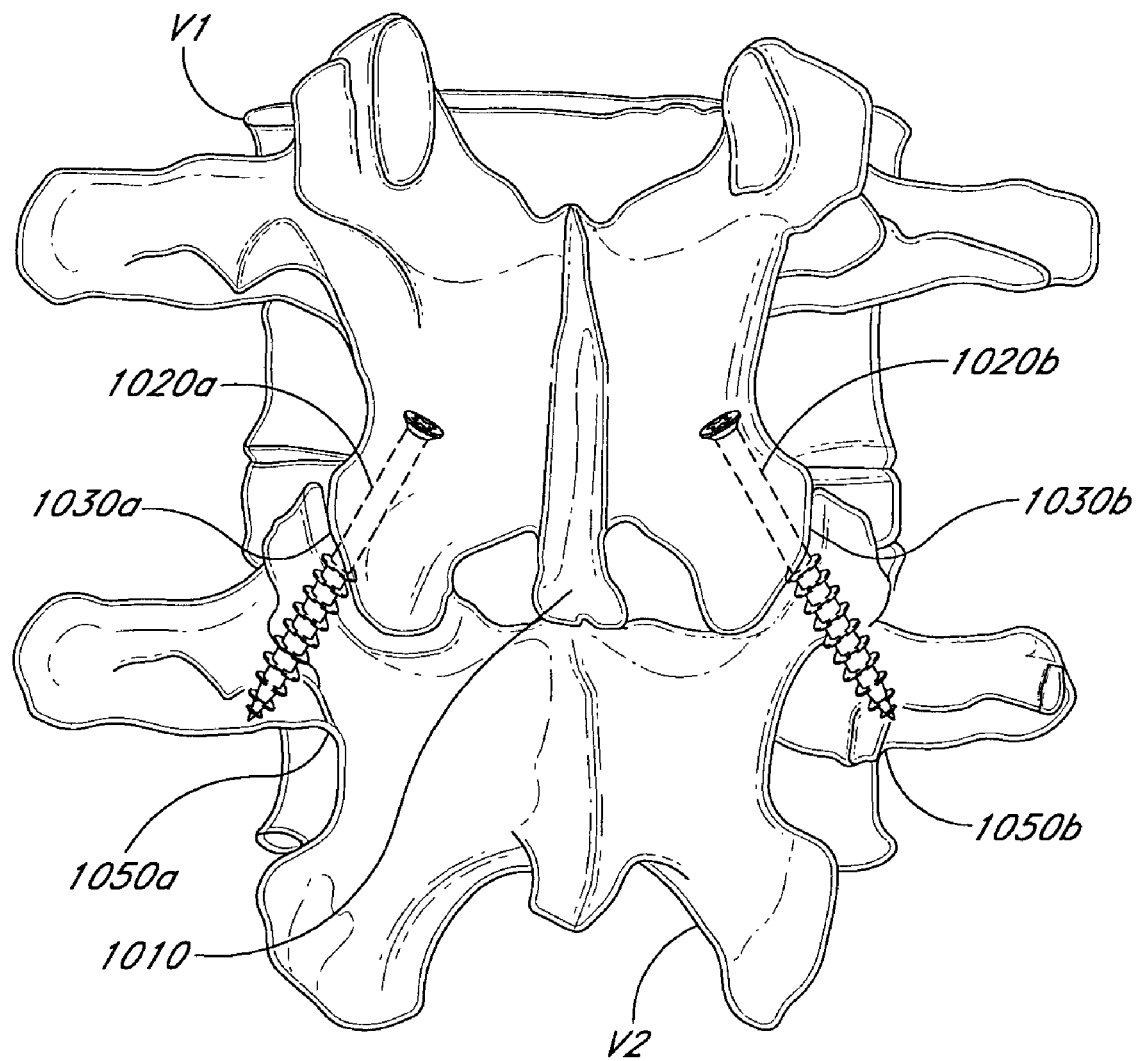
FIG. 47 is a view illustrating one embodiment of a fixation method.

With the access device oriented as described above, the doctor can then stabilize the vertebrae using transfacet pedicle screw fixation. FIGS. 45-47 illustrate how the vertebrae are stabilized using transfacet pedicle screw fixation. Two fasteners 1020a and 1020b are used to secure the vertebrae. In a preferred embodiment, the physician will initiate the procedure by accessing the spine through the access device 20 and scoring the bone on the facet joint with a drill, wire, probe, or some other similar device known in the art to offer a starting point for insertion of the fasteners. In one embodiment, the bone through which the fasteners are to run may be optionally tapped, pre-drilled or marked in some other manner to allow for ease and accuracy when inserting the fasteners. In a preferred embodiment, the bone is scored at the entry point to the facet joint and the fasteners 1020a and 1020b are inserted without a pre-drilled hole.

Once a starting point has been marked, the physician can, though an access device 20, introduce a first fastener 1020a to the desired vertebrae. This fastener 1020a is secured through the facet joint 1030a into the base 1050a of the pedicle of the second vertebrae V2 using a screw driver or similar device D2 passing through the access device 20 and coming into mechanical contact with the fastener 1020a. Because of the second, expanded configuration at the distal end of the access device 20, a second fastener 1020b is similarly secured through the same access device 20 on the side opposite the first fastener 1020a, travelling through the facet joint 1030b into the base 1050b of the pedicle of the second vertebrae V2. The angle of the access device 20 may be altered laterally as needed to facilitate insertion of the fasteners. These fasteners 1020a and 1020b may comprise screws, straight pins or tapered pins pressed into or bonded to the bone such that they travel through the two vertebrae securing them together. In addition, said fasteners 1020a and 1020b may be composed of a number of biocompatible, stiff materials, including metal material, polymeric material, ceramic material, or other synthetic or naturally stiff material with similar characteristics. In a preferred embodiment, the fasteners 1020a and 1020b are screws made of a metallic material. Transfacet pedicle screw fixation is further described in an article by H. Boucher entitled "Method of spinal fusion." *Clin Orthop* 1997; 335; 4-9, the entirety of which is hereby incorporated by reference.

In another embodiment, two access devices are used to accomplish the transfacet pedicle screw fixation. FIG. 46 shows an example of how the access devices 20 might be placed to accomplish such a fixation. The exact angle is determined by the spinal structure and the angle required to insert the fasteners 1020a and 1020b into the bone. In this embodiment, each access device 20 may enter from a generally posterior approach and rests at or near the desired facet joint, preferably at a first angle A1 of approximately 0 to 60 from the S-P plane, a second angle A2 of approximately 0 to 60 from the T-P plane, and a third angle A3 (not shown) of approximately 0 to 90 from the S-T plane. More preferably, the first angle A1 is approximately 15 to 45 from S-P plane, the second angle A2 is 15 to 45 from the T-P plane, and the third angle A3 is 40 to 80 from the S-T plane. These angles are largely determined by the structure of the individual spine that the doctor addresses in each operation and should not be considered strict requirements for this embodiment.

As described above, the bone through which the fasteners are to run may be optionally tapped, pre-drilled or marked in some other manner to allow for ease and accuracy when inserting the fasteners. In a preferred embodiment, the fasteners provide the stabilization required to allow the bone of the adjacent vertebrae to fuse. In one embodiment of this stabilization technique, a single insertion point through the back and a single access device are used to conduct the entire operation to further minimize the trauma to surrounding tissue in the region of the desired stabilization. Though a narrow cannula may provide access for insertion of a single fastener, the access device described herein allows the necessary room to insert several fasteners at angles to each other. It should be noted that though a single access device may be used, multiple access devices may be used to facilitate the operation.

It is to be understood that the fixation techniques herein described may be used in combination with any number of other spinal operations, including but not limited to discectomy, nucleotomy, laminectomy, laminotomy, distraction, postero-lateral fusion, etc.

Further details of the expandable conduit and its applications are described in U.S. patent application Ser. No. 10/658,736, filed Sep. 9, 2003, which is herein incorporated by reference in its entirety.

It will be understood that the foregoing is only illustrative of the principles of the invention, and that various modifications, alterations, and combinations can be made by those skilled in the art without departing from the scope and spirit of the invention.

What is claimed is:

1. A method of fixing adjoining vertebrae of the spine of a patient, comprising:
    inserting into said patient a single access device to a surgical location adjacent the spine with said access device in a first configuration having a first cross-sectional area at a distal portion thereof, said access device having a proximal portion pivotably attached to a distal portion;
    actuating said access device to a second configuration having an enlarged cross-sectional area at said distal portion thereof, such that said distal portion provides access to two or more facet joints;
    delivering a first fastener through the access device to the surgical location;
    advancing said first fastener through a first vertebra and into a second vertebra through a first facet joint;
    pivoting the proximal portion of said access device relative to the distal portion to change the angle of the access device to facilitate insertion of a second fastener;
    delivering said second fastener through said access device to the surgical location; and
    advancing said second fastener through said first vertebra and into said second vertebra through a second facet joint.

2. The method of claim 1, wherein the access device is inserted via a generally posterior approach.

3. The method of claim 1, wherein the access device is inserted via a postero-lateral approach.

4. The method of claim 1, further comprising the introduction of a boring tool to the surgical location through the access device and advancing said boring tool to create a first tunnel through the first and second vertebra at the first facet joint prior to delivering said first fastener.

5. The method of claim 4, further comprising prior to delivering said second fastener, introducing said boring tool through the access device and advancing said boring tool to create a second tunnel through the first and second vertebra at the second facet joint.

6. The method of claim 1, wherein the bone of the first facet joint is scored prior delivering the first fastener or boring through the bone.

7. The method of claim 1, wherein the method of fixation is transfacet pedicle screw fixation.

8. The method of claim 1, wherein the method of fixation is translaminar facet screw fixation.

9. The method of claim 1, wherein said second facet joint is scored prior to delivering said second fastener or boring through the bone.

10. The method of claim 1, wherein the proximal portion of said access device relative to the distal portion is pivoted between a longitudinal axis of the access device and the plane that is generally perpendicular to the spine at an angle that is less than about 60 degrees.

11. The method of claim 1, wherein the proximal portion of said access device relative to the distal portion is pivoted between a longitudinal axis of the access device and the plane that is generally perpendicular to the spine at an angle that is in a range from about 10 degrees to about 45 degrees.

12. A method of treating a spine of a patient, comprising:
    inserting a first access device into said patient to a surgical location adjacent the spine with said first access device positioned on a first side of spinous processes of first and second vertebrae, said first access device in a first configuration having a first cross-sectional area at a distal portion thereof, said first access device having a proximal portion pivotably attached to a distal portion;
    actuating said first access device to a second configuration having an enlarged cross-sectional area at said distal portion thereof;
    pivoting the proximal portion of said first access device relative to the distal portion to provide access to at least a first facet joint;
    inserting a second access device into said patient to a second surgical location adjacent the spine with said second access device positioned on a second side of spinous processes of said first and second vertebrae, said second access device in a first configuration having a first cross-sectional area at a distal portion thereof, said second access device having a proximal portion pivotably attached to a distal portion;
    actuating said second access device to a second configuration having an enlarged cross-sectional area at said distal portion thereof;
    pivoting the proximal portion of said second access device relative to the distal portion to provide access to at least a second facet joint;
    fastening a first fastener through the first vertebra and into the second vertebra through the first facet joint, said first fastener delivered through said first access device; and
    fastening a second fastener though the first vertebra and into the second vertebra though the second facet joint, said second fastener delivered though said second access device, said first and second fasteners providing a transfacet fixation method substantially preventing movement of the first vertebra relative to the second vertebra.

13. The method of claim 12, wherein the first and second access devices are inserted via a generally posterior approach.

14. The method of claim 12, wherein the first and second access devices are inserted via a postero-lateral approach.

15. The method of claim 12, wherein the proximal portion of said first access device relative to the distal portion is pivoted between a longitudinal axis of the first access device and the plane that is generally perpendicular to the spine at an angle that is less than about 60 degrees.

16. The method of claim 12, wherein the proximal portion of said first access device relative to the distal portion is pivoted between a longitudinal axis of the first access device and the plane that is generally perpendicular to the spine at an angle that is in a range from about 10 degrees to about 45 degrees.

17. The method of claim 12, wherein the proximal portion of said second access device relative to the distal portion is pivoted between a longitudinal axis of the second access device and the plane that is generally perpendicular to the spine at an angle that is less than about 60 degrees.

18. The method of claim 12, wherein the proximal portion of said second access device relative to the distal portion is pivoted between a longitudinal axis of the second access device and the plane that is generally perpendicular to the spine at an angle that is in a range from about 10 degrees to about 45 degrees.

19. A method of fixing adjoining vertebrae of the spine of a patient, comprising:
   inserting into said patient a single access device with said access device in a first configuration having a first cross-sectional area at a distal portion thereof, said access device having a proximal portion pivotably attached to a distal portion;
   actuating said access device to a second configuration having an enlarged cross-sectional area at said distal portion thereof exposing a first surgical location adjacent the spine and a second surgical location adjacent the spine, wherein said access device is positioned such that a spinous process of at least a first vertebra is within or adjacent a working space defined by the distal end of the access device in the second configuration;
   delivering a first fastener through the access device to the first surgical location at a first facet joint;
   advancing said first fastener through a first vertebra and into a second vertebra at the first facet joint;
   pivoting the proximal portion of the access device relative to the distal portion to provide access to a second facet joint;
   delivering a second fastener to the second surgical location at the second facet joint through the access device; and
   advancing the second fastener through the first vertebra and into the second vertebra at the second facet joint, said first and second fasteners substantially preventing movement of the first vertebra relative to the second vertebra.

20. The method of claim 19, wherein the spinous process of the first vertebra is within the working space.

21. The method of claim 19, wherein the spinous process of the second vertebra is within the working space.

22. The method of claim 19, wherein the spinous process of a third vertebra is within the working space.

23. The method of claim 19, wherein the spinous process of the first vertebra is accessible through a working space defined by the distal end of the access device in the second configuration.

24. A method of performing a translaminar fixation of adjoining vertebrae of the spine of a patient, comprising:
   inserting into said patient an access device having a medial side to a first surgical location on a first side of the spine, the access device having a first cross-sectional area at a distal portion thereof during insertion, the first access device having a proximal portion pivotably attached to the distal portion;
   actuating said access device such that said distal portion has an enlarged cross-sectional area, wherein during said actuating said medial side of the access device moves toward the spinous process of a first vertebra;
   pivoting the proximal portion of the access device relative to the distal portion to provide access along a line extending through the spinous process and through the facet joint on a second side of the spine;
   delivering a first fastener through the access device to the surgical location; and
   advancing said first fastener through the spinous process of the first vertebra and into a second vertebra through a first facet joint.

25. The method of claim 24, further comprising delivering a second fastener through the access device to the surgical location and advancing the second fastener through the spinous process of the first vertebra and into a second vertebra through a second facet joint.

26. The method of claim 25, wherein the second fastener is delivered and advanced though a second access device positioned on a second side of the spine.

* * * * *

UNITED STATES PATENT AND TRADEMARK OFFICE
CERTIFICATE OF CORRECTION

PATENT NO. : 7,731,737 B2 Page 1 of 1
APPLICATION NO. : 10/693663
DATED : June 8, 2010
INVENTOR(S) : Gene DiPoto It is certified that error appears in the above-identified patent and that said Letters Patent is hereby corrected as shown below:

Column 26
Line 55, 56, and 57 delete "though", and insert therefor -- through --.

Column 28
Line 42 delete "though", and insert therefor -- through --.

Signed and Sealed this

Third Day of August, 2010

David J. Kappos
*Director of the United States Patent and Trademark Office*